(12) United States Patent  
Sun

(10) Patent No.: US 12,279,904 B2  
(45) Date of Patent: Apr. 22, 2025

(54) MEDICAL DEVICES AND CONTROL SYSTEMS THEREOF

(71) Applicant: SHANGHAI UNITED IMAGING HEALTHCARE CO., LTD., Shanghai (CN)

(72) Inventor: Biao Sun, Shanghai (CN)

(73) Assignee: SHANGHAI UNITED IMAGING HEALTHCARE CO., LTD., Shanghai (CN)

( * ) Notice: Subject to any disclaimer, the term of this patent is extended or adjusted under 35 U.S.C. 154(b) by 630 days.

(21) Appl. No.: 17/455,939

(22) Filed: Nov. 22, 2021

(65) Prior Publication Data

US 2022/0079546 A1 Mar. 17, 2022

Related U.S. Application Data

(63) Continuation of application No. PCT/CN2020/091666, filed on May 21, 2020.

(30) Foreign Application Priority Data

| May 21, 2019 | (CN) | ......................... 201910422442.8 |
| Dec. 28, 2019 | (CN) | ......................... 201911383373.0 |
| Mar. 17, 2020 | (CN) | ......................... 202010186070.6 |

(51) Int. Cl.
*A61B 6/00* (2024.01)
*A61B 6/04* (2006.01)
(Continued)

(52) U.S. Cl.
CPC ............ *A61B 6/547* (2013.01); *A61B 6/0407* (2013.01); *A61B 6/102* (2013.01); *A61B 6/4441* (2013.01); *A61B 6/461* (2013.01); *A61B 6/467* (2013.01)

(58) Field of Classification Search
CPC ....... A61B 6/547; A61B 6/0407; A61B 6/102; A61B 6/4441; A61B 6/461; A61B 6/467;
(Continued)

(56) References Cited

U.S. PATENT DOCUMENTS

| 7,340,409 B1 | 3/2008 | Ulwick |
| 2004/0008688 A1 | 1/2004 | Matsubara et al. |

(Continued)

FOREIGN PATENT DOCUMENTS

| CN | 2751349 Y | 1/2006 |
| CN | 201435082 Y | 3/2010 |

(Continued)

OTHER PUBLICATIONS

The Extended European Search Report in European Application No. 20808884.9 mailed on May 31, 2022, 7 pages.

(Continued)

*Primary Examiner* — Courtney D Thomas
(74) *Attorney, Agent, or Firm* — METIS IP LLC

(57) ABSTRACT

The present disclosure provides a medical device and a control system. The control system may achieve a motion control of the medical device: obtaining a target position of the medical device, determining a target motion path of the medical device according to a current position and the target position of the medical device, and controlling the medical device to move from the current position to the target position along the target motion path. The control system may also perform an information registration control method for the medical device: obtaining load change information related to the medical device, and determining an operation instruction related to a registration record of the medical device based on the load change information and a preset change condition. The medical device may include a radiation source, a detector, a C-arm, and a display.

17 Claims, 16 Drawing Sheets

(51) Int. Cl.
*A61B 6/10* (2006.01)
*A61B 6/46* (2024.01)

(58) Field of Classification Search
CPC ..... A61B 5/1115; A61B 5/6844; A61B 5/704;
A61B 2562/0247; A61B 6/0487; A61B
6/03; A61B 6/032; A61B 6/037; A61B
6/0492; A61B 2562/0252; A61B 6/12;
A61B 6/4435; A61B 6/4476; A61B 6/54;
A61B 6/545; A61B 5/055; G16H 30/20;
G16H 40/63
See application file for complete search history.

(56) References Cited

U.S. PATENT DOCUMENTS

| | | | |
|---|---|---|---|
| 2006/0215817 | A1 | 9/2006 | Watanabe |
| 2009/0070939 | A1 | 3/2009 | Hann |
| 2013/0243160 | A1 | 9/2013 | Graumann et al. |
| 2017/0347979 | A1* | 12/2017 | Fehre .................. A61B 6/4441 |
| 2018/0310901 | A1 | 11/2018 | Garlow et al. |
| 2018/0322110 | A1 | 11/2018 | Rhodes et al. |
| 2019/0053774 | A1 | 2/2019 | Weingarten |
| 2019/0126463 | A1 | 5/2019 | Purushothaman |

FOREIGN PATENT DOCUMENTS

| | | | |
|---|---|---|---|
| CN | 202288286 | U | 7/2012 |
| CN | 203102361 | U | 7/2013 |
| CN | 203182923 | U | 9/2013 |
| CN | 104463622 | A | 3/2015 |
| CN | 104665858 | A | 6/2015 |
| CN | 205041418 | U | 2/2016 |
| CN | 105719043 | A | 6/2016 |
| CN | 106157210 | A | 11/2016 |
| CN | 106361022 | A | 2/2017 |
| CN | 206224578 | U | 6/2017 |
| CN | 107252353 | A | 10/2017 |
| CN | 107797749 | A | 3/2018 |
| CN | 108055026 | A | 5/2018 |
| CN | 108549424 | A | 9/2018 |
| CN | 109472538 | A | 3/2019 |
| CN | 109598327 | A | 4/2019 |
| CN | 109671497 | A | 4/2019 |
| CN | 109801007 | A | 5/2019 |
| CN | 110123350 | A | 8/2019 |
| CN | 110459318 | A | 11/2019 |
| CN | 111053565 | A | 4/2020 |
| DE | 102010062090 | B4 | 6/2016 |
| JP | 2002351986 | A | 12/2002 |
| WO | 2017056476 | A1 | 4/2017 |

OTHER PUBLICATIONS

Royal Philips, Azurion Version 1.1: Philips Instructions for Use, Wiki, 2016, 744 pages.
International Search Report in PCT/CN2020/091666 mailed on Aug. 10, 2020, 5 pages.
Written Opinion in PCT/CN2020/091666 mailed on Aug. 10, 2020, 6 pages.
First Office Action in Chinese Application No. 201911383373.0 mailed on Sep. 30, 2020, 12 pages.
First Office Action in Chinese Application No. 202010186070.6 mailed on Mar. 29, 2021, 9 pages.
First Office Action in Chinese Application No. 201910422442.8 mailed on Feb. 19, 2021, 15 pages.

* cited by examiner

MEDICAL DEVICES AND CONTROL SYSTEMS THEREOF

CROSS-REFERENCE TO RELATED APPLICATIONS

This application is a Continuation of International Application No. PCT/CN2020/091666 filed on May 21, 2020, which claims priority of Chinese Patent Application No. 201911383373.0, filed on Dec. 28, 2019, Chinese Patent Application No. 202010186070.6, filed on Mar. 17, 2020, and Chinese Patent Application No. 201910422442.8, filed on May 21, 2019, the contents of which are hereby incorporated by reference.

TECHNICAL FIELD

One or more embodiments of the disclosure relate to medical devices, in particular to a medical device and a control system thereof.

BACKGROUND

With the development of science and technology, medical devices play an increasingly important role in the medical field, such as detection, diagnosis, and surgery. However, the control of the medical device mainly depends on the manual operation of medical staff, for example, manually moving the medical device to a detection position. This may require the medical staff to spend a lot of time in controlling the position of the medical device. In addition, it may also require that the medical staff are well experienced.

Therefore, it is desired to provide a medical device and a control system that may efficiently and accurately control the medical device.

SUMMARY

One or more embodiments of the present disclosure provide a motion control method of a medical device. The method may include: obtaining a target position of the medical device, determining a target motion path of the medical device based on a current position and the target position of the medical device, and controlling the medical device moving from the current position to the target position along the target motion path.

In some embodiments, the medical device may include a C-arm device. The C-arm device may include a gantry and a C-arm connected to the gantry. The target position of the medical device may include a target position of the gantry or a target position of the C-arm.

In some embodiments, when the medical device may include a C-arm device, the method may further include: obtaining the target position to which the user expects the C-arm device to move, determining the target motion path of the C-arm device based on the current position and the target position of the C-arm device, and controlling the C-arm device to move from the current position to the target position along the target motion path.

In some embodiments, the obtaining the target position of the medical device may be implemented through a graphical user interface GUI displayed on an operation console.

In some embodiments, the obtaining the target position may include: outputting a three-dimensional planning view through the GUI, and receiving the target position input or selected by the user in the three-dimensional planning view.

In some embodiments, the method for obtaining the target position through the GUI displayed on the operation console may include: determining the target position according to an operation of a device icon representing the medical device in the three-dimensional planning view. The operation may include a dragging operation or a rotation operation.

In some embodiments, the method may further include obtaining a prohibited operation region. In some embodiments, determining the target motion path may include: determining the target motion path of the medical device according to the current position, the target position, and the prohibited operation region of the medical device.

In some embodiments, the target motion path may be a fixed path or a dynamic path. The dynamic path may be a path that needs to be adjusted according to a real-time spatial image.

In some embodiments, the spatial image may be taken by a camera disposed in the medical device or a treatment room.

In some embodiments, one or more embodiments of the present disclosure provide a motion control device for the medical device. The device may include an acquisition module, a target motion path determination module, and a motion control module. The acquisition module may be configured to obtain the target position of the medical device. The target motion path determination module may be configured to determine the target motion path of the medical device according to the current position and the target position of the medical device. The motion control module may be configured to control the medical device to move from the current position to the target position along the target motion path.

One or more embodiments of the present disclosure provide a motion control system for the medical device. The system may include a catheter bed, a C-arm device, an operation console, and a processor. The catheter bed may be configured to carry a patient to receive a diagnosis and treatment. The C-arm device may include a gantry, and a C-arm connected to the gantry. One end of the C-arm may be disposed with a radiation source and another end of the C-arm may be disposed with a detector. The radiation source may be configured to emit rays, and the detector may be configured to receive rays passing through the patient on the catheter bed. The operation console may be configured to obtain the target position of the medical device. The processor may be configured to determine the target motion path of the medical device according to the current position and the target position of the medical device; and control the medical device to move from the current position to the target location along the target motion path.

One or more embodiments of the present disclosure provide a storage medium including computer-executable instructions. The computer-executable instructions, when executed by a computer processor, may be used to execute the motion control method as described above.

One or more embodiments of the present disclosure provide an information registration control method for the medical device. The method may include obtaining load change information related to the medical device, and determining an operation instruction related to a registration record of the medical device based on the load change information and a preset change condition.

In some embodiments, in response to that the load change information satisfies the preset change condition, it may be determined that the operation instruction is to close the registered registration record or pop up a registration record to be entered.

In some embodiments, the load change information may include pressure change information or mass change information.

In some embodiments, the load change information may include the pressure change information. The obtaining load change information related to the medical device may include obtaining the pressure change information generated by a load change of a bed caused by loading or unloading the patient. The determining an operation instruction related to a registration record of the medical device based on the load change information and a preset change condition may include: when the pressure change information satisfies a preset pressure change condition, closing a registration record of an unloaded patient, or popping up a registration record for a current patient, so that an information registration of the current patient may be performed.

In some embodiments, the preset pressure change condition may include a preset positive pressure change condition. The determining an operation instruction related to a registration record of the medical device based on the load change information and a preset change condition may include: when the pressure change information satisfies the preset positive pressure change condition, popping up the registration record to be entered for the current patient.

In some embodiments, the popping up the registration record to be entered for the current patient may include: directly popping up the registration record to be entered for the current patient, or closing the registration record of the previous unloaded patient, and simultaneously popping up the registration record for the current patient.

In some embodiments, the preset pressure change condition may include a preset negative pressure change condition, wherein it is determined whether the pressure change information satisfies the preset negative pressure change condition before closing the registration record of the unloaded patient. In response to that a time interval between the pressure change information from satisfying the preset negative pressure change condition to satisfying the preset positive pressure change condition does not exceed a preset time threshold, the registration record of the unloaded patient may not be closed or the registration record to be entered may be popped up. In response to that the preset time threshold is exceeded, the registration record of the unloaded patient may be closed and the registration record to be entered may be popped up.

In some embodiments, the preset pressure change condition may include the preset negative pressure change condition. The determining an operation instruction related to a registration record of the medical device based on the load change information and a preset change condition may include: when the pressure change information satisfies the preset negative pressure change condition, closing the registration record for the unloaded patient.

In some embodiments, before obtaining the pressure change information generated by the load change of the bed caused by loading or unloading the patient, the method may further include obtaining weight information of the patient and determining the preset pressure change condition according to the weight information.

In some embodiments, the method may be used in a digital subtraction angiography system, a computed tomography system, a nuclear magnetic resonance imaging system, a digital X-ray imaging system, a positron emission tomography system, a single-photon emission computed tomography system, or a dual-mode scanning system.

One or more embodiments of the present disclosure provide an information registration control device for the medical device. The information registration control device for the medical device may include a change information acquisition module and an operation instruction determination module. The change information obtaining module may be configured to obtain the load change information related to the medical device. The operation instruction determination module may be configured to determine the operation instruction related to the registration record of the medical device based on the load change information and the preset change condition.

One or more embodiments of the present disclosure provide an information registration control system for the medical device. The information registration control system may include a bed, a pressure detection device, an imaging device, and a processor. The bed may be configured to carry the patient. The pressure detection device may be configured to detect the pressure change information generated by loading or unloading the patient and causing the change in the load of the bed. The imaging device may be disposed on one side of the bed, and configured to obtain medical images of the current patient according to an obtained signal. The processor may be configured to receive the pressure change information detected by the pressure detection device generated by the load change of the bed caused by loading or unloading the patient, and close the registration record of the unloaded patient when the pressure change information satisfies the preset pressure change condition, or pop up the registration record in the state to be entered for the current patient, so that the information registration of the current patient may be performed, and the imaging device may be controlled to obtain the medical image of the current patient when the obtaining signal is detected.

In some embodiments, the registration control system may also include an operator console. The operation console may be configured to display the registration record.

In some embodiments, the registration control system may be used in a digital subtraction angiography system, a computed tomography system, a nuclear magnetic resonance imaging system, a digital X-ray photography system, a positron emission tomography system, a single-photon emission computed tomography system, or a dual-modal scanning system.

One or more embodiments of the present disclosure provide a storage medium including computer-executable instructions. The computer-executable instructions, when executed by a computer processor, may be configured to execute the information registration control method as described above.

One or more embodiments of the present disclosure provide a C-arm device. The C-arm device may include a radiation source, a detector, a C-arm, and a display. The detector may be disposed at one end of the C-arm. The radiation source may be disposed at another end of the C-arm and opposite to the detector. The display may be configured to display parameter configuration information and/or operation parameter information related to the C-arm, and the display may be disposed on the C-arm.

In some embodiments, the C-arm device may further include a C-arm slide rail. The display may be disposed on the C-arm slide rail or the C-arm.

In some embodiments, the C-arm device may further include a support arm and a connection portion. The display may be disposed on at least one of the support arm, the connection portion, and the C-arm.

In some embodiments, the parameter configuration information may include at least one of time information, device information, and patient information. The operation parameter information may include at least one of information such as angle information of the C-arm, height information of a bed surface, collision information, a distance between the radiation source and an imaging surface of the detector, status information of related devices, power information of the display, and image information.

In some embodiments, the display may also be configured to display at least one of the angle information of the C-arm, the height information of the bed surface, the collision information, and the distance between the radiation source and the imaging surface of the detector.

In some embodiments, the display may also be configured to display at least one of the time information, the device information, the patient information, and the generated image information.

In some embodiments, the display may also be configured to display the collision information, the status information of related devices, or the power information of the display.

In some embodiments, the display may further include a sound playing module. The sound playing module may be configured to play a sound, wherein the sound may include music and/or voice.

In some embodiments, the display may further include an indicator light. The indicator light may be configured to indicate the collision information, the status information of the display, or the power information of the display.

In some embodiments, the display may further include a touch screen. The touch screen may be configured to receive touch instructions input by the user. The touch instruction may be used to: control the angle of the C-arm, control the height of the bed surface of the bed, control the display of the image information, adjust the brightness of the display, or control display state of the touch screen.

In some embodiments, the C-arm device may further include a rotating column and a rail. One end of the rotating column may be rotatably connected to the support arm. The rail and another end of the rotating column may be slidably connected.

In some embodiments, the C-arm device may further include a base. One end of the base may be connected to the support arm.

Additional features will be set forth in part in the description which follows, and in part will become apparent to those skilled in the art upon examination of the following and the accompanying drawings or may be learned by production or operation of the examples. The features of the present disclosure may be realized and attained by practice or use of various aspects of the methodologies, instrumentalities, and combinations set forth in the detailed examples discussed below.

BRIEF DESCRIPTION OF THE DRAWINGS

The present disclosure is further described in terms of exemplary embodiments. These exemplary embodiments are described in detail with reference to the drawings. The drawings are not scaled. These embodiments are non-limiting exemplary embodiments, in which like reference numerals represent similar structures throughout the several views of the drawings, and wherein.

DETAILED DESCRIPTION

Figure 1:
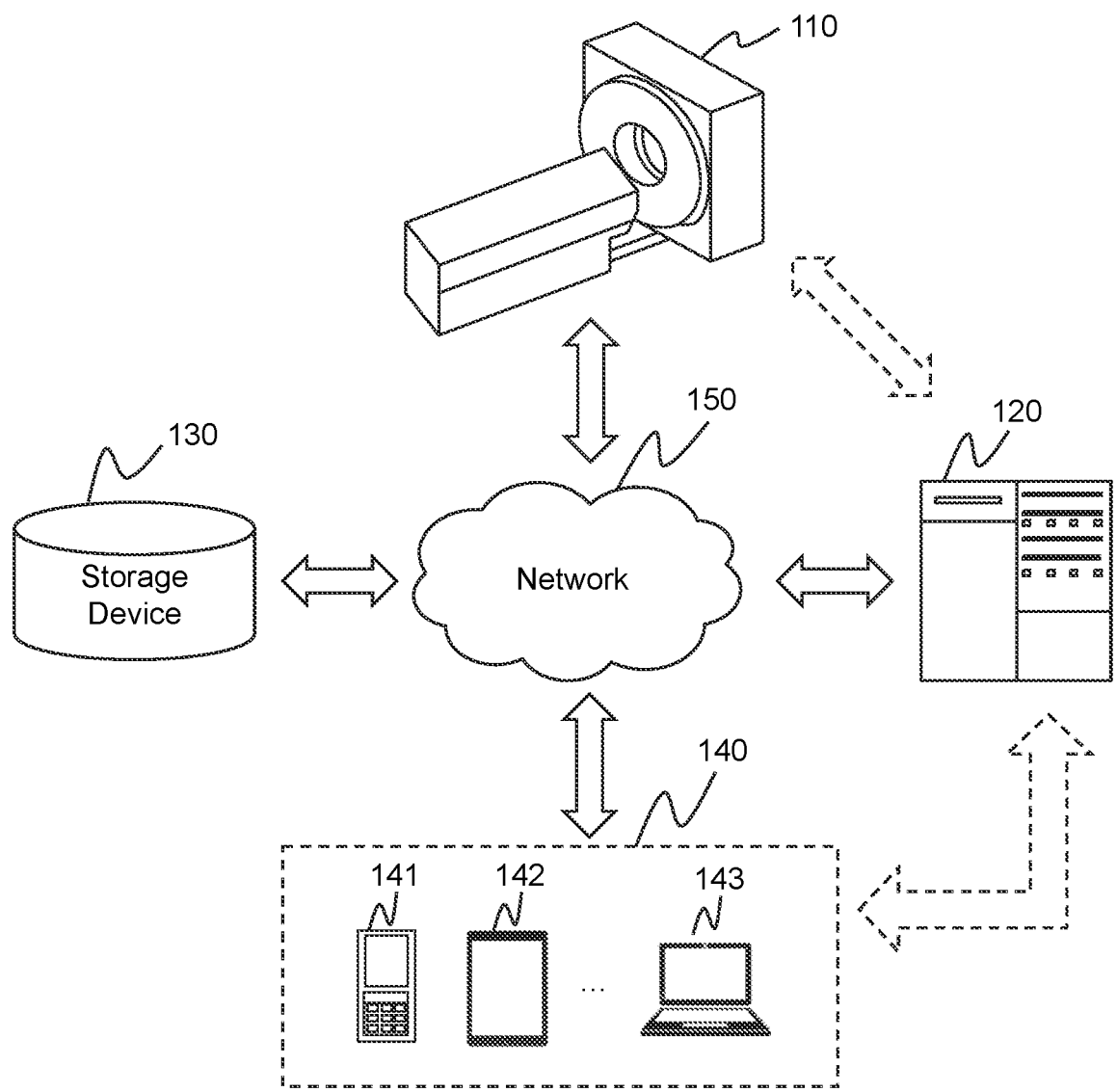
FIG. 1 is a schematic diagram illustrating an exemplary medical system according to some embodiments of the present disclosure.

The following description is presented to enable any person skilled in the art to make and use the present disclosure and is provided in the context of a particular application and its requirements. Various modifications to the disclosed embodiments will be readily apparent to those skilled in the art, and the general principles defined herein may be applied to other embodiments and applications without departing from the spirit and scope of the present disclosure. Thus, the present disclosure is not limited to the embodiments shown but is to be accorded the widest scope consistent with the claims.

The terminology used herein is for the purpose of describing particular example embodiments only and is not intended to be limiting. As used herein, the singular forms "a," "an," and "the" may be intended to include the plural forms as well, unless the context clearly indicates otherwise. It will be further understood that the terms "comprise,"

"comprises," and/or "comprising," "include," "includes," and/or "including" when used in this disclosure, specify the presence of stated features, integers, steps, operations, elements, and/or components, but do not preclude the presence or addition of one or more other features, integers, steps, operations, elements, components, and/or groups thereof.

Generally, the word "module," "unit," or "block," as used herein, refers to logic embodied in hardware or firmware, or to a collection of software instructions. A module, a unit, or a block described herein may be implemented as software and/or hardware and may be stored in any type of non-transitory computer-readable medium or other storage devices. In some embodiments, a software module/unit/block may be compiled and linked into an executable program. It will be appreciated that software modules can be callable from other modules/units/blocks or themselves, and/or may be invoked in response to detected events or interrupts. Software modules/units/blocks configured for execution on computing devices may be provided on a computer-readable medium, such as a compact disc, a digital video disc, a flash drive, a magnetic disc, or any other tangible medium, or as a digital download (and can be originally stored in a compressed or installable format that needs installation, decompression, or decryption prior to execution). Such software code may be stored, partially or fully, on a storage device of the executing computing device, for execution by the computing device. Software instructions may be embedded in firmware, such as an erasable programmable read-only memory (EPROM). It will be further appreciated that hardware modules/units/blocks may be included in connected logic components, such as gates and flip-flops, and/or can be included of programmable units, such as programmable gate arrays or processors. The modules/units/blocks or computing device functionality described herein may be implemented as software modules/units/blocks but may be represented in hardware or firmware. In general, the modules/units/blocks described herein refer to logical modules/units/blocks that may be combined with other modules/units/blocks or divided into sub-modules/sub-units/sub-blocks despite their physical organization or storage. The description may be applicable to a system, an engine, or a portion thereof.

It will be understood that the term "system," "engine," "unit," "module," and/or "block" used herein are one method to distinguish different components, elements, parts, sections, or assembly of different levels in ascending order. However, the terms may be displaced by another expression if they achieve the same purpose.

It will be understood that when a unit, engine, module or block is referred to as being "on," "connected to," or "coupled to," another unit, engine, module, or block, it may be directly on, connected or coupled to, or communicate with the other unit, engine, module, or block, or an intervening unit, engine, module, or block may be present unless the context clearly indicates otherwise. As used herein, the term "and/or" includes any and all combinations of one or more of the associated listed items.

These and other features, and characteristics of the present disclosure, as well as the methods of operation and functions of the related elements of structure and the combination of parts and economies of manufacture, may become more apparent upon consideration of the following description regarding the accompanying drawings, all of which form a part of this disclosure. It is to be expressly understood, however, that the drawings are for the purpose of illustration and description only and are not intended to limit the scope of the present disclosure. It is understood that the drawings are not to scale.

The flowcharts used in the present disclosure illustrate operations that systems implement according to some embodiments in the present disclosure. It is to be expressly understood, the operations of the flowchart may be implemented not in order. Conversely, the operations may be implemented in an inverted order, or simultaneously. Moreover, one or more other operations may be added to the flowcharts. One or more operations may be removed from the flowcharts.

A medical device may be a basic condition for continuously improving the level of medical science and technology, and an important symbol of modernization. With the continuous progress of science and technology, the use of medical device becomes more and more convenient. For example, the medical device may move to a target position quickly according to a motion control process. Moreover, the display displayed on the medical device may accurately display a motion position of the medical device, a distance from the target position, and/or a deviation from the target position. As another example, after the medical device moves to the target position and the patient lies on a catheter bed of the medical device for detection, the medical device may automatically perform an information registration for the patient through the sensor, thereby effectively solving the problem of unregistering a new patient or the problem that the patient has not been logged out. In addition, through the display disposed on the medical device, the information registration result may be accurately displayed.

FIG. 1 is a schematic diagram illustrating an exemplary medical system 100 according to some embodiments of the present disclosure. As shown, the medical system 100 may include a medical imaging device 110, a processing device 120, a storage device 130, one or more terminals 140, and a network 150. In some embodiments, the medical imaging device 110, the processing device 120, the storage device 130, and/or the terminal(s) 140 may be connected to and/or communicate with each other via a wireless connection, a wired connection, or a combination thereof. The connection between the components of the medical system 100 may be variable. Merely by way of example, the medical imaging device 110 may be connected to the processing device 120 through the network 150 or directly. As a further example, the storage device 130 may be connected to the processing device 120 through the network 150 or directly.

The medical imaging device 110 may generate or provide image data related to a target subject via scanning the target subject. For illustration purposes, image data of a target subject acquired using the medical imaging device 110 is referred to as medical image data. In some embodiments, the target subject may include a biological subject and/or a non-biological subject. For example, the target subject may include a specific portion of a body, such as the head, the thorax, the abdomen, or the like, or a combination thereof. As another example, the target subject may be a man-made composition of organic and/or inorganic matters that are with or without life. In some embodiments, the medical system 100 may include modules and/or components for performing imaging and/or related analysis. In some embodiments, the medical image data relating to the target subject may include projection data, one or more images of the target subject, etc. The projection data may include raw data generated by the medical imaging device 110 by scanning the target subject and/or data generated by a forward projection on an image of the target subject.

In some embodiments, the medical imaging device 110 may be a non-invasive biomedical medical imaging device for disease diagnostic or research purposes. The medical imaging device 110 may include a single modality scanner and/or a multi-modality scanner. The single modality scanner may include, for example, an ultrasound scanner, an X-ray scanner, an computed tomography (CT) scanner, a magnetic resonance imaging (MRI) scanner, an ultrasonography scanner, a positron emission tomography (PET) scanner, an optical coherence tomography (OCT) scanner, an ultrasound (US) scanner, an intravascular ultrasound (IVUS) scanner, a near-infrared spectroscopy (NIRS) scanner, a far-infrared (FIR) scanner, or the like, or any combination thereof. The multi-modality scanner may include, for example, an X-ray imaging-magnetic resonance imaging (X-ray-MRI) scanner, a positron emission tomography-X-ray imaging (PET-X-ray) scanner, a single-photon emission computed tomography-magnetic resonance imaging (SPECT-MRI) scanner, a positron emission tomography-computed tomography (PET-CT) scanner, a digital subtraction angiography-magnetic resonance imaging (DSA-MRI) scanner, etc. It should be noted that the scanner described above is merely provided for illustration purposes, and not intended to limit the scope of the present disclosure. The term "imaging modality" or "modality" as used herein broadly refers to an imaging method or technology that gathers, generates, processes, and/or analyzes imaging information of a target subject.

The processing device 120 may process data and/or information obtained from the medical imaging device 110, the storage device 130, and/or the terminal (s) 140. For example, the processing device 120 may obtain a target location of the medical device, determine a target motion path of the medical device according to a current position and the target position of the medical device, and control the medical device to move from the current position to the target position along the target motion path. For another example, the processing device 120 may acquire load change information related to the medical device, and determine an operation instruction related to a registration record of the medical device based on the load change information and a preset change condition.

In some embodiments, the processing device 120 may be a single server or a server group. The server group may be centralized or distributed. In some embodiments, the processing device 120 may be local to or remote from the medical system 100. For example, the processing device 120 may access information and/or data from the medical imaging device 110, the storage device 130, and/or the terminal(s) 140 via the network 150. As another example, the processing device 120 may be directly connected to the medical imaging device 110, the terminal(s) 140, and/or the storage device 130 to access information and/or data. In some embodiments, the processing device 120 may be implemented on a cloud platform. For example, the cloud platform may include a private cloud, a public cloud, a hybrid cloud, a community cloud, a distributed cloud, an inter-cloud, a multi-cloud, or the like, or a combination thereof. In some embodiments, the processing device 120 may be implemented by a computing device 200 having one or more components as described in connection with FIG. 2.

In some embodiments, the processing device 120 may include one or more processors (e.g., single-core processor(s) or multi-core processor(s)). Merely by way of example, the processing device 120 may include a central processing unit (CPU), an application-specific integrated circuit (ASIC), an application-specific instruction-set processor (ASIP), a graphics processing unit (GPU), a physics processing unit (PPU), a digital signal processor (DSP), a field-programmable gate array (FPGA), a programmable logic device (PLD), a controller, a microcontroller unit, a reduced instruction set computer (RISC), a microprocessor, or the like, or any combination thereof.

The storage device 130 may store data, instructions, and/or any other information. In some embodiments, the storage device 130 may store data obtained from the processing device 120, the terminal(s) 140, and/or the medical imaging device 110. In some embodiments, the storage device 130 may store data and/or instructions that the processing device 120 may execute or use to perform exemplary methods described in the present disclosure. In some embodiments, the storage device 130 may include a mass storage device, a removable storage device, a volatile read-and-write memory, a read-only memory (ROM), or the like, or any combination thereof. Exemplary mass storage devices may include a magnetic disk, an optical disk, a solid-state drive, etc. Exemplary removable storage devices may include a flash drive, a floppy disk, an optical disk, a memory card, a zip disk, a magnetic tape, etc. Exemplary volatile read-and-write memory may include a random access memory (RAM). Exemplary RAM may include a dynamic RAM (DRAM), a double date rate synchronous dynamic RAM (DDR SDRAM), a static RAM (SRAM), a thyristor RAM (T-RAM), and a zero-capacitor RAM (Z-RAM), etc. Exemplary ROM may include a mask ROM (MROM), a programmable ROM (PROM), an erasable programmable ROM (EPROM), an electrically erasable programmable ROM (EEPROM), a compact disk ROM (CD-ROM), and a digital versatile disk ROM, etc. In some embodiments, the storage device 130 may be implemented on a cloud platform as described elsewhere in the disclosure.

In some embodiments, the storage device 130 may be connected to the network 150 to communicate with one or more other components of the medical system 100 (e.g., the processing device 120, the terminal(s) 140). One or more components of the medical system 100 may access the data or instructions stored in the storage device 130 via the network 150. In some embodiments, the storage device 130 may be part of the processing device 120.

The terminal(s) 140 may enable user interaction between a user and the medical system 100. For example, the terminal(s) 140 may display a graphical user interface (GUI) to determine the target position. In some embodiments, the terminal(s) 140 may include a mobile device 141, a tablet computer 142, a laptop computer 143, or the like, or any combination thereof. For example, the mobile device 141 may include a mobile phone, a personal digital assistant (PDA), a gaming device, a navigation device, a point of sale (POS) device, a laptop, a tablet computer, a desktop, or the like, or any combination thereof. In some embodiments, the terminal(s) 140 may include an input device, an output device, etc. In some embodiments, the terminal(s) 140 may be part of the processing device 120.

The network 150 may include any suitable network that can facilitate the exchange of information and/or data for the medical system 100. In some embodiments, one or more components of the medical system 100 (e.g., the medical imaging device 110, the processing device 120, the storage device 130, the terminal(s) 140) may communicate information and/or data with one or more other components of the medical system 100 via the network 150. For example, the processing device 120 may obtain medical image data from the medical imaging device 110 via the network 150.

As another example, the processing device 120 may obtain user instruction(s) from the terminal(s) 140 via the network 150.

The network 150 may be or include a public network (e.g., the Internet), a private network (e.g., a local area network (LAN)), a wired network, a wireless network (e.g., an 802.11 network, a Wi-Fi network), a frame relay network, a virtual private network (VPN), a satellite network, a telephone network, routers, hubs, switches, server computers, and/or any combination thereof. For example, the network 150 may include a cable network, a wireline network, a fiber-optic network, a telecommunications network, an intranet, a wireless local area network (WLAN), a metropolitan area network (MAN), a public telephone switched network (PSTN), a Bluetooth™ network, a ZigBee™ network, a near field communication (NFC) network, or the like, or any combination thereof. In some embodiments, the network 150 may include one or more network access points. For example, the network 150 may include wired and/or wireless network access points such as base stations and/or internet exchange points through which one or more components of the medical system 100 may be connected to the network 150 to exchange data and/or information.

It should be noted that the above description of the medical system 100 is intended to be illustrative, and not to limit the scope of the present disclosure. Many alternatives, modifications, and variations will be apparent to those skilled in the art. The features, structures, methods, and other characteristics of the exemplary embodiments described herein may be combined in various ways to obtain additional and/or alternative exemplary embodiments. For example, the medical system 100 may include one or more additional components. Additionally or alternatively, one or more components of the medical system 100, such as the medical imaging device 110 described above may be omitted. As another example, two or more components of the medical system 100 may be integrated into a single component. Merely by way of example, the processing device 120 (or a portion thereof) may be integrated into the medical imaging device 110.

Figure 2:
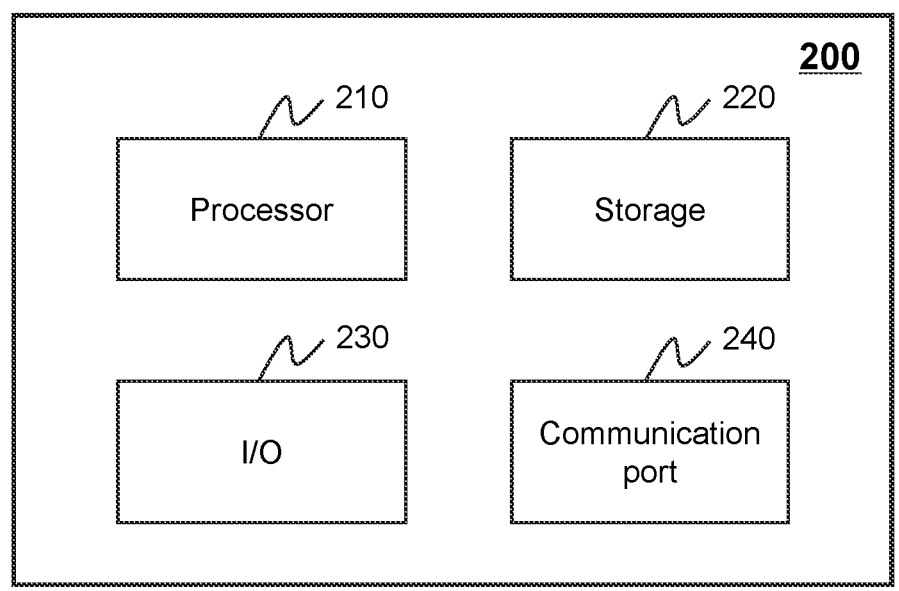
FIG. 2 is a schematic diagram illustrating exemplary hardware and/or software components of a computing device according to some embodiments of the present disclosure.

FIG. 2 is a schematic diagram illustrating exemplary hardware and/or software components of a computing device 200 according to some embodiments of the present disclosure. The computing device 200 may be used to implement any component of the medical system 100 as described herein. For example, the processing device 120 and/or the terminal 140 may be implemented on the computing device 200, respectively, via its hardware, software program, firmware, or a combination thereof. Although only one such computing device is shown, for convenience, the computer functions relating to the medical system 100 as described herein may be implemented in a distributed fashion on a number of similar platforms, to distribute the processing load. As illustrated in FIG. 2, the computing device 200 may include a processor 210, a storage device 220, an input/output (I/O) 230, and a communication port 240.

The processor 210 may execute computer instructions (e.g., program code) and perform functions of the processing device 120 in accordance with techniques described herein. The computer instructions may include, for example, routines, programs, subjects, components, data structures, procedures, modules, and functions, which perform particular functions described herein. For example, the processor 210 may process image data obtained from the medical imaging device 110, the terminal(s) 140, the storage device 130, and/or any other component of the medical system 100. In some embodiments, the processor 210 may include one or more hardware processors, such as a microcontroller, a microprocessor, a reduced instruction set computer (RISC), an application specific integrated circuits (ASICs), an application-specific instruction-set processor (ASIP), a central processing unit (CPU), a graphics processing unit (GPU), a physics processing unit (PPU), a microcontroller unit, a digital signal processor (DSP), a field-programmable gate array (FPGA), an advanced RISC machine (ARM), a programmable logic device (PLD), any circuit or processor capable of executing one or more functions, or the like, or any combinations thereof.

Merely for illustration, only one processor is described in the computing device 200. However, it should be noted that the computing device 200 in the present disclosure may also include multiple processors, thus operations and/or method operations that are performed by one processor as described in the present disclosure may also be jointly or separately performed by the multiple processors. For example, if in the present disclosure the processor of the computing device 200 executes both operation A and operation B, it should be understood that operation A and operation B may also be performed by two or more different processors jointly or separately in the computing device 200 (e.g., a first processor executes operation A and a second processor executes operation B, or the first and second processors jointly execute operations A and B).

The storage device 220 may store data/information obtained from the medical imaging device 110, the terminal(s) 140, the storage device 130, and/or any other component of the medical system 100. In some embodiments, the storage device 220 may include a mass storage device, a removable storage device, a volatile read-and-write memory, a read-only memory (ROM), or the like, or any combination thereof. In some embodiments, the storage device 220 may store one or more programs and/or instructions to perform exemplary methods described in the present disclosure. For example, the storage device 220 may store a program for the processing device 120 to execute to perform a motion control of a medical device.

The I/O 230 may input and/or output signals, data, information, etc. In some embodiments, the I/O 230 may enable a user interaction with the processing device 120. In some embodiments, the I/O 230 may include an input device and an output device. The input device may include alphanumeric and other keys that may be input via a keyboard, a touch screen (for example, with haptics or tactile feedback), a speech input, an eye-tracking input, a brain monitoring system, or any other comparable input mechanism. The input information received through the input device may be transmitted to another component (e.g., the processing device 120) via, for example, a bus, for further processing. Other types of the input device may include a cursor control device, such as a mouse, a trackball, or cursor direction keys, etc. The output device may include a display (e.g., a liquid crystal display (LCD), a light-emitting diode (LED)-based display, a flat panel display, a curved screen, a television device, a cathode ray tube (CRT), a touch screen), a speaker, a printer, or the like, or a combination thereof.

The communication port 240 may be connected to a network (e.g., the network 150) to facilitate data communications. The communication port 240 may establish connections between the processing device 120 and the medical imaging device 110, the terminal(s) 140, and/or the storage device 130. The connection may be a wired connection, a wireless connection, any other communication connection that can enable data transmission and/or reception, and/or any combination of these connections. The wired connection may include, for example, an electrical cable, an optical cable, a telephone wire, or the like, or any combination thereof. The wireless connection may include, for example, a Bluetooth™ link, a Wi-Fi™ link, a WiMax™ link, a WLAN link, a ZigBee™ link, a mobile network link (e.g., 3G, 4G, 5G), or the like, or a combination thereof. In some embodiments, the communication port 240 may be and/or include a standardized communication port, such as RS232, RS485, etc. In some embodiments, the communication port 240 may be a specially designed communication port. For example, the communication port 240 may be designed in accordance with the digital imaging and communications in medicine (DICOM) protocol.

Figure 3:
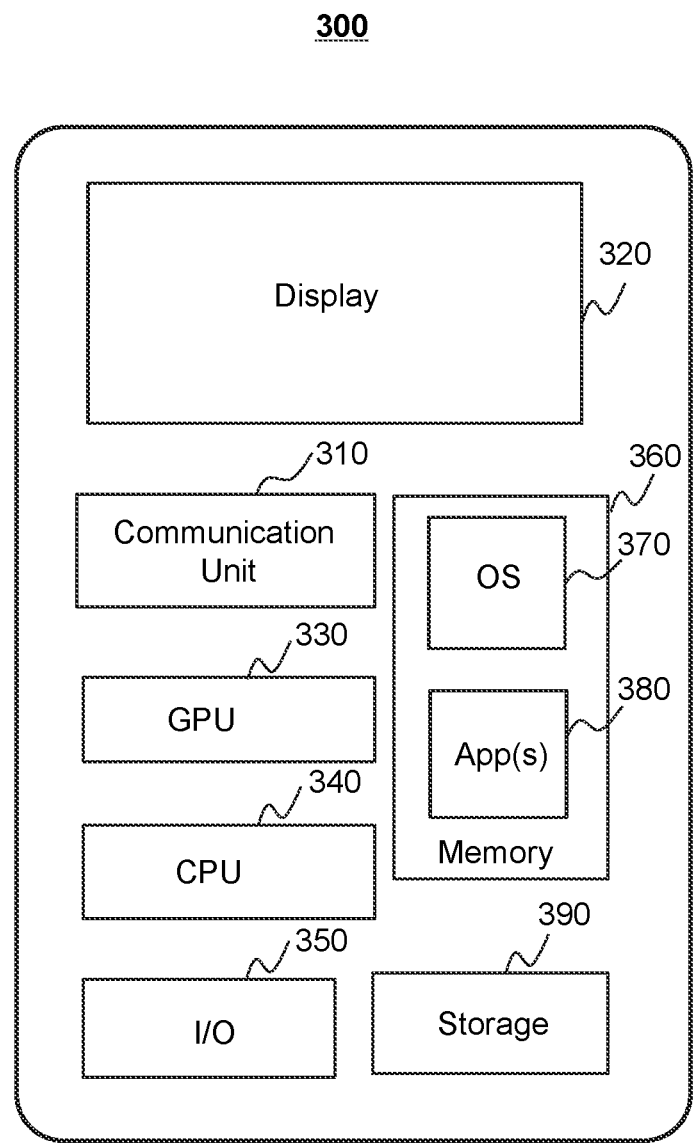
FIG. 3 is a schematic diagram illustrating exemplary hardware and/or software components of a mobile device according to some embodiments of the present disclosure.

FIG. 3 is a schematic diagram illustrating exemplary hardware and/or software components of a mobile device 300 according to some embodiments of the present disclosure. In some embodiments, one or more components (e.g., a terminal 140 and/or the processing device 120) of the medical system 100 may be implemented on the mobile device 300.

As illustrated in FIG. 3, the mobile device 300 may include a communication platform 310, a display 320, a graphics processing unit (GPU) 330, a central processing unit (CPU) 340, an I/O 350, a memory 360, and storage 390. In some embodiments, any other suitable component, including but not limited to a system bus or a controller (not shown), may also be included in the mobile device 300. In some embodiments, a mobile operating system 370 (e.g., iOS™, Android™, Windows Phone™) and one or more applications 380 may be loaded into the memory 360 from the storage 390 in order to be executed by the CPU 340. The applications 380 may include a browser or any other suitable mobile apps for receiving and rendering information relating to the medical system 100. User interactions with the information stream may be achieved via the I/O 350 and provided to the processing device 120 and/or other components of the medical system 100 via the network 150.

To implement various modules, units, and their functionalities described in the present disclosure, computer hardware platforms may be used as the hardware platform(s) for one or more of the elements described herein. A computer with user interface elements may be used to implement a personal computer (PC) or any other type of work station or terminal device. A computer may also act as a server if appropriately programmed.

During a treatment process, it is necessary to move a gantry of a medical device to a preset position to image a patient, and reset the gantry after the imaging is completed. In some embodiments, medical staff may be required to manually move the gantry to the preset position before the imaging begins. During the motion, it may be necessary to avoid collision between the gantry and a catheter bed. Therefore, it may be necessary for the medical staff to repeatedly adjust the position of the gantry. The operation efficiency may be low, and the adjustment time of the gantry may usually depend on the experience of the medical staff. In some embodiments, a motion control process of the medical device may be provided to implement a motion control and rapid automatic positioning of the medical device.

Figure 4:
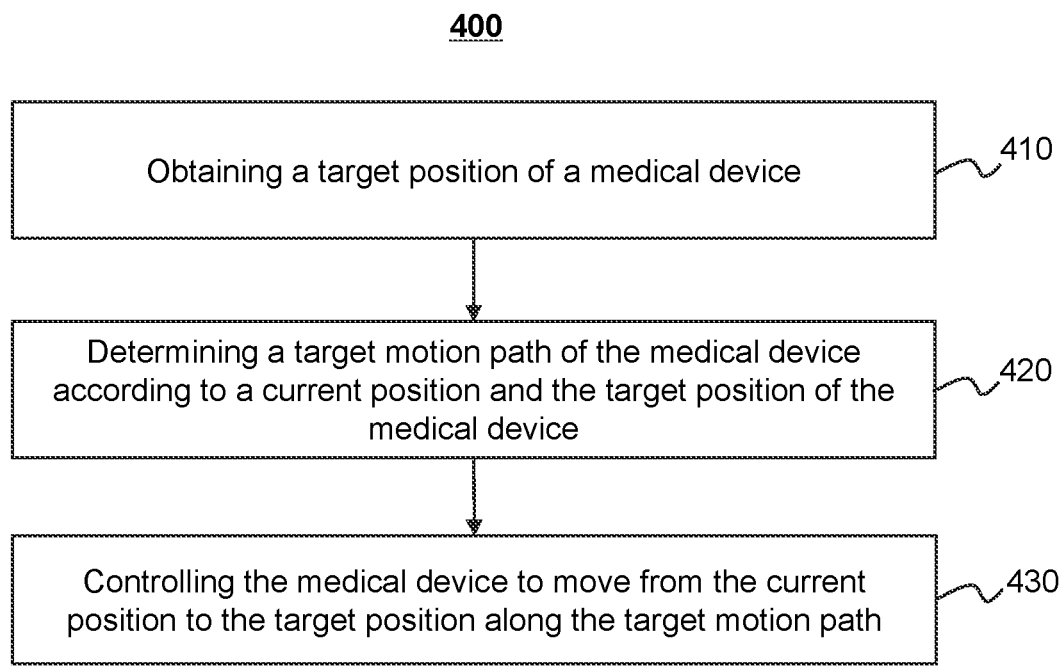
FIG. 4 is a flowchart illustrating a motion control process according to some embodiments of the present disclosure.

FIG. 4 is a flowchart illustrating a motion control process according to some embodiments of the present disclosure. The technical solution of the embodiment may be suitable for the case where a medical device is automatically moved from a current position to a target position according to a clinic requirement. The process 400 may be executed by a motion control device according to the embodiment of the present disclosure. The process 400 may be implemented in software and/or hardware, e.g., the processing device 120. The process 400 may include one or more of the following operations.

In 410, the processing device 120 may obtain the target position of the medical device.

The medical device may be a medical device for imaging a patient. In some embodiments, the medical device may include a C-arm device. The C-arm device may include a gantry and a C-arm connected to the gantry. In some embodiments, the gantry may include a mobile gantry, a suspended gantry, a robot arm, or the like. One end of the C-arm may be disposed with a radiation source, and another end of the C-arm may be disposed with a flat panel detector. In some embodiments, the medical device may further include an X-ray scanner, a computed tomography (CT) scanner, a magnetic resonance imaging (MRI) scanner, a positron emission tomography (PET) scanner, or the like, or any combination thereof. More descriptions regarding the medical device may be found in FIG. 1, and the descriptions thereof.

In some embodiments, after an imaging operation of each patient by the medical device is completed, the gantry of the medical device may need to be moved to a target position away from a catheter bed, for example, an initial position of the medical device, a position where the patient is not susceptible to a collision, etc. And when using the medical device to image a new patient on the catheter bed, the medical device may need to be moved to a target position near the catheter bed according to the actual situation of the new patient. In addition, an imaging angle may still need to be adjusted, that is, the radiation source and the flat panel detector of the medical device may be rotated to their target positions. Therefore, before moving the medical device, one or more target positions of the medical device may need to be obtained.

The target position of the medical device may include a target position of at least one of the gantry, the C-arm, the radiation source, and the flat panel detector. In some embodiments, if only the entire medical device needs to be moved to the target position, the target position of the medical device may be regarded as the target position of any element on the entire medical device. For example, the target position of the medical device may be the target position of the gantry, the target position of the radiation source, and/or the target position of the flat panel detector. In some embodiments, if a position adjustment of a component of the medical device is required, the target position of the medical device may include the target position of the local element for position adjustment. For example, when the detector or radiation source are required to move to a specific position, the target position of the medical device may include the specific position of the radiation source or the flat panel detector. In some embodiments, the target position may be understood as a position to which the user expects the medical device or one or more components thereof to move.

To facilitate obtaining the target position of the medical device, the processing device 120 may provide the user with a planning view of a current treatment room through a graphical user interface (GUI) of an operation console. Therefore, the user may directly input or select the target position in the planning view displayed by the GUI. The planning view may be a schematic view drawn according to positions of all objects in the current treatment room. In some embodiments, the planning view may include a two-dimensional planning view or a three-dimensional planning view. In some embodiments, the GUI may be understood as a computer-operated user interface displayed in a graphical manner, for example, an operation interface of an application corresponding to the medical device. In some embodiments, the GUI may be presented to the user through a display screen of the operating console of the medical device.

In some embodiments, the user may select the target position by clicking or double-clicking a desired position in the planning view. In some embodiments, the user may be understood as a medical worker or a person who operates the medical device.

In some embodiments, the user may input or select the target position by dragging or rotating a device icon representing the medical device in the planning view.

For example, the user may move the device icon from the current position to the target position by dragging in the planning view. As used herein, the current position may be a non-operation position, and the corresponding target position may be an operation position; or the current position may be an operation position, and the corresponding target position may be a non-operation position. The operation position may be a position where the user operates the medical device to perform a medical operation. In some embodiments, the medical operation may include a treatment operation (e.g., a surgical operation, a radiotherapy operation, etc.), or a detection operation (e.g., a CT imaging detection). Correspondingly, in some embodiments, the operation position may include a position capable of performing the relevant treatment operation or detection operation on the patient, for example, a position adjacent to the catheter bed, a position adjacent to the bed for CT imaging. The non-operating position may be a position where the medical device is not operated for any medical operation. For example, the position may be a position away from the catheter bed, the initial position of the medical device, a position away from the patient, etc.

As another example, the user may rotate the device icon from the current position to the target position in the planning view. As used herein, the current position and the target position may be both operating positions, and the rotation operation is suitable for adjusting a scanning angle of the radiation source during a treatment process. In some embodiments, the current position and the target position may be both non-operating positions, and the rotation operation is suitable for adjusting the radiation source for homing.

It may be understood that, in some embodiments, the drag of the device icon may correspond to a translation of the radiation source, and the rotation of the device icon may correspond to a rotation (e.g., change of the scanning angle) of the radiation source. In some embodiments, the drag of the device icon may correspond to a change in a translation of the flat panel detector, and the rotation of the device icon may correspond to a rotation (e.g., change in a scanning angle) of the flat panel detector.

In some embodiments, the display screen of the console may be a touch screen. Therefore, the user may select the target position by dragging or rotating the device icon in the three-dimensional planning view. In some embodiments, the user may also select the target position in the planning view by clicking on the touch screen.

In 420, the processing device 120 may determine a target motion path of the medical device according to the current position and the target position of the medical device.

The current position of the medical device may refer to a position before a motion of the medical device. In some embodiments, the current location of the medical device may be obtained in real time. For example, the current location may be obtained in real time by a position detection device of the medical device. The current position of the medical device may include the current position of at least one of the gantry, the C-arm, the radiation source, and the flat panel detector.

In some embodiments, the medical device may include a gantry rail. The gantry may move along the gantry rail. In some embodiments, the gantry rail may be a rail disposed on the ground. In some embodiments, the gantry rail may be a guide rail suspended in the air. In a process of determining the target motion path, if the medical device includes a gantry rail and the medical device (e.g. the gantry) is required to move along the gantry rail, the target motion path of the gantry may be determined after obtaining the current position and the target position of the gantry. Under normal circumstances, the gantry and/or the radiation source may not collide with other objects during moving along the gantry rail.

In some embodiments, it may be necessary to move the radiation source from the current position to the target position by dragging the gantry. At this time, the motion path of the radiation source may include not only the gantry rail, but also other routes distributed outside the gantry rail. Therefore, a prohibited operation region may be obtained. After the prohibited operation region and the target position are determined, the target motion path of the gantry may be determined according to the current position, the target position, and the prohibited operation region of the gantry. As used herein, the prohibited operation region may be a region where the gantry may collide during moving, for example, a region where an object such as the catheter bed, the display screen, etc. is placed.

It may be understood that if the spatial arrangement of the treatment room does not change, the prohibited operation region may be fixed. In this case, the prohibited operation region may be stored in a memory and can be directly retrieved each time that the target motion path is determined.

In some embodiments, the target motion path may be a straight path connecting the current position and the target position of the medical device (e.g., the C-arm device), or a compound path connecting the current position and the target position of the medical device, wherein the compound path may be composed of multiple single paths mutually connected. In addition, the target motion path may only include a straight path, or the target motion path may also include a curved path. In some embodiments, to improve the stability of the motion of the gantry, the target motion path may preferably include only straight paths. The target motion path may be obtained through a target motion path determination module. In the target motion path determination module, for example, a principle with the shortest total motion or other principles (e.g., the smallest count of the single paths) may be used to determine the path.

In some embodiments, the target motion path may further include a rotation path of at least one of the C-arm, the radiation source, and the flat panel detector. For example, the user may need to adjust the radiation source or detector to a desired angular position according to the rotation path. In some embodiments, the target motion path may be a composite motion path. The composite motion path may include a gantry motion path and a rotation path of at least one of the C-arm, the radiation source, and the flat panel detector. In some embodiments, the user may instruct the medical device to move to the target position through the gantry motion path and the rotation path of at least one of the C-arm, the radiation source, and the flat panel detector. For example, the user may instruct the gantry to move from the current position to a first target position (i.e., the target position of the gantry) through the gantry movement path, and further instruct the radiation source to move to a second target position (i.e., the target position of the radiation source) through the rotation path, thereby moving the medical device from the current position to the target position.

In 430, the processing device 120 may control the medical device to move from the current position to the target position along the target motion path.

After the target motion path of the gantry is determined, the medical device (e.g., the gantry, the C-arm, the radiation source, and/or the flat panel detector) may be controlled to automatically move from the current position to the target position along the target motion path without the need for a user to manually adjust the position of the medical device, which achieves a technical effect of simplifying the imaging operation process of the medical device.

The technical solution of the motion control process according to the embodiments of the present disclosure may determine the target motion path of the medical device according to the current position and target position of the medical device, and control the medical device moving from the current position to the target position along the target motion path after the target moving path is determined. The embodiments may achieve the technical effect of automatically adjusting the position of the medical device, without the need for the user to manually adjust the position, thereby simplifying the operation process of the medical device and improving the operating experience of the user.

Figure 5:
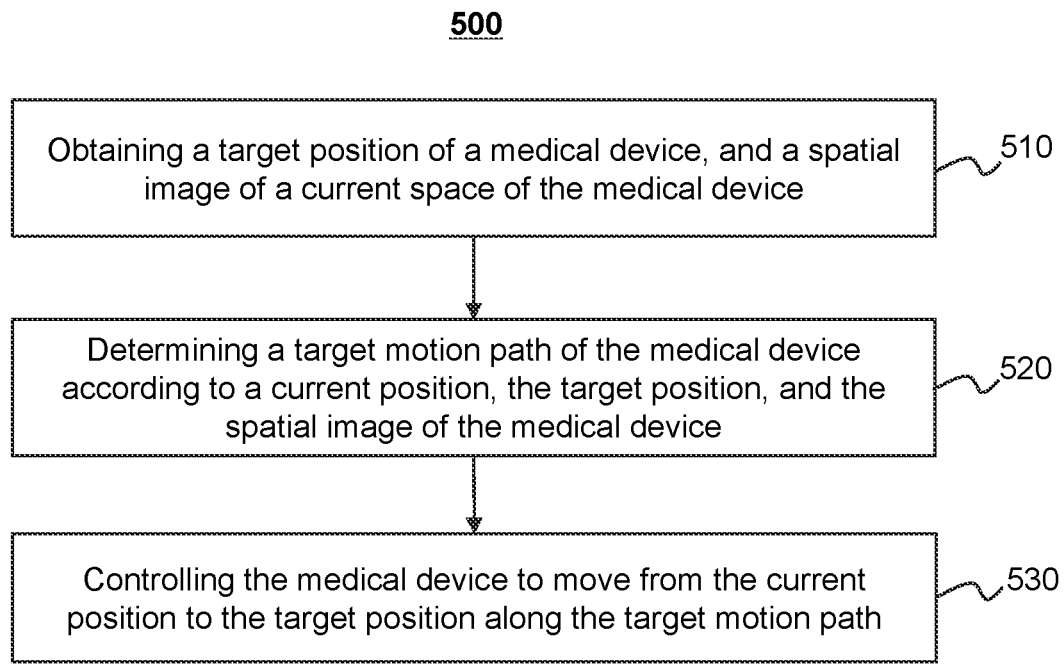
FIG. 5 is a flowchart illustrating a motion control process according to another embodiment of the present disclosure.

FIG. 5 is a flowchart illustrating a motion control process according to another embodiment of the present disclosure. The embodiment of the present disclosure may add an operation of optimizing the target motion path based on the above embodiment. Correspondingly, as shown in FIG. 5, the motion control process may include one or more of the following operations.

In 510, the processing device 120 may obtain a target position of a medical device, and a spatial image of a current space of the medical device.

The current space may refer to space where the medical device is located, for example, a space of a treatment room, a space of an examination room, or the like. Preferably, the target motion path corresponding to a position adjustment of the medical device may be a path in a three-dimensional space. If the spatial arrangement of the treatment room changes frequently, a prohibited operation region may often change. To find a better or optimal target motion path, in the embodiment, while obtaining the target position of the medical device, the spatial image of the current space of the medical device may be obtained to determine a spatial distribution of the treatment room according to the spatial image, thereby determining the prohibited operation region.

The spatial image may include a static spatial image, a dynamic spatial image (i.e., a video), or the like. In some embodiments, the spatial image may be acquired in real time. The spatial image may be acquired by a camera installed in the medical device or the treatment room. The count of cameras may be one or more, as long as the spatial distribution of the possible motion path of the medical device may be obtained. In some embodiments, the camera may be placed at any position on a gantry, a C-arm, an operating console, etc., of the medical device.

In 520, the processing device 120 may determine a target motion path of the medical device according to a current position, the target position, and the spatial image of the medical device.

The target motion path of the medical device may be determined according to the current position, the target position, and the spatial image of the medical device. As used herein, the target motion path may be a fixed path or a dynamic path. The fixed path may be a determined full path that may not be adjusted during the operation of the medical device. The dynamic path may be a path optimized in real time. The optimization of the dynamic path may be based on the real-time spatial image, and follow the anti-collision and the shortest path principle, so that the medical device may quickly move from the current position to the target position.

In 530, the processing device 120 may control the medical device to move from the current position to the target position along the target motion path.

Since the space image includes the spatial distribution of the space where the medical device is located, the prohibited operation region of the medical device may be determined according to the space image. The target motion path that avoids collision of the medical device may be obtained according to the current position, the target position, and the prohibited operation region of the medical device. After the target motion path is determined, the medical device may be controlled to automatically move from the current position to the target position along the target motion path without the need for manual adjustment by a user, thereby simplifying the imaging operation process of the medical device.

Figure 6:
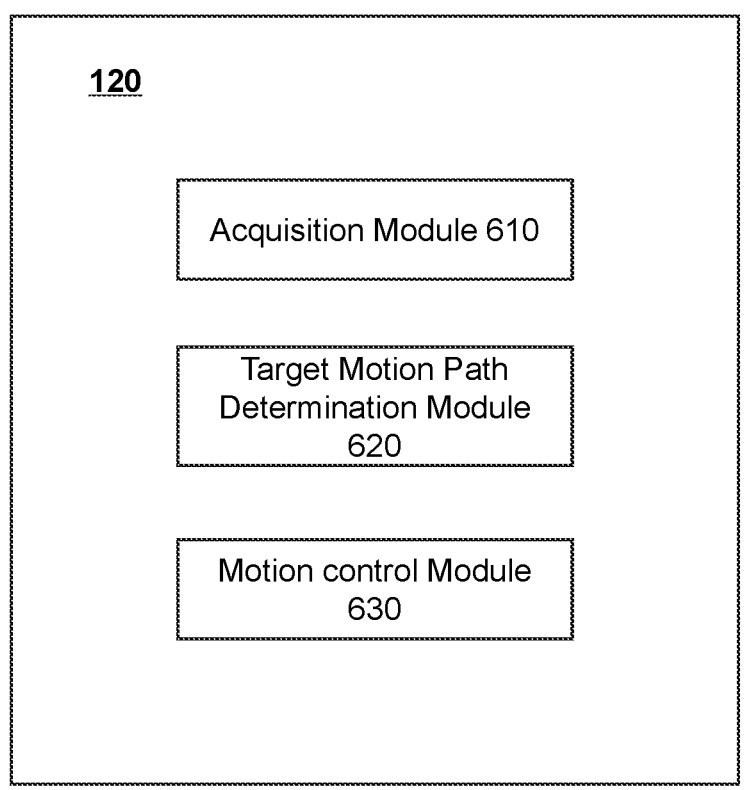
FIG. 6 is a structural block diagram illustrating a motion control device according to some embodiments of the present disclosure.

FIG. 6 is a structural block diagram illustrating a motion control device according to some embodiments of the present disclosure. The motion control device may be used to perform the motion control process according to any of the above embodiments. The motion control device may be implemented in software or hardware. As shown in FIG. 6, the device may include an acquisition module 610, a target motion path determination module 620, and a motion control module 630.

The acquisition module 610 may be used to obtain a target position of a medical device.

The target motion path determination module 620 may be used to determine a target motion path of the medical device according to a current position and the target position of the medical device.

The motion control module 630 may be used to control the medical device to move from the current position to the target position along the target motion path.

In some embodiments, the acquisition module 610 may obtain the target position of the medical device through a graphical user interface (GUI) displayed on an operation console.

In some embodiments, the obtaining module 610 may output a three-dimensional planning view through the GUI, and receive the target position input by the user in the three-dimensional planning view.

In some embodiments, the obtaining module 610 may determine the target position according to an operation of a device icon representing the medical device in the three-dimensional planning view. The operation may include a dragging operation or a rotation operation.

In some embodiments, the target motion path may be a fixed path or a dynamic path. The dynamic path may be a path that needs to be adjusted according to a real-time spatial image.

In some embodiments, the spatial image may be taken by a camera disposed in the medical device or a treatment room.

In some embodiments, the obtaining module 610 may be also used to obtain a prohibited operation region. The target motion path determination module 620 may be also used to determine the target motion path of the medical device based on the current position, the target position, and the prohibited operation region of the medical device.

The motion control device according to the embodiment of the present invention may obtain the target position of the medical device through an acquisition module, determine the target motion path of the medical device according to the current position and the target position of the medical device through the target motion path determination module, and control the medical device to move from the current position to the target position along the target motion path through the motion control module 630. The motion control device may automatically adjust the position of the medical device without a doctor manually adjusting the position of the medical device, which helps to simplify an operation process of the medical device and improve the operation experience of a user.

Figure 7:
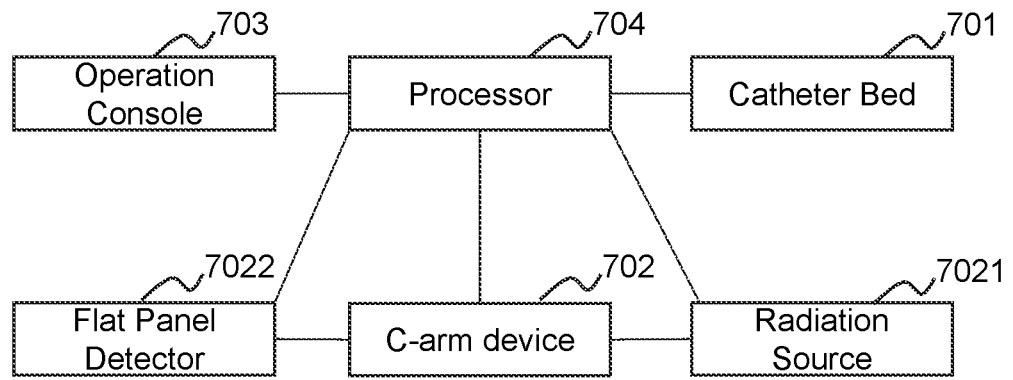
FIG. 7 is a structural block diagram illustrating a motion control system for a medical device according to some embodiments of the present disclosure.

FIG. 7 is a structural block diagram illustrating a motion control system of a medical device according to some embodiments of the present disclosure. The medical device may be described by taking a C-arm device as an example. As shown in FIG. 7, the motion control system may include a catheter bed 701, a C-arm device 702, an operation console 703, and a processor 704. The catheter bed 701 may be used to carry a patient undergoing medical treatment. The C-arm device 702 may include a gantry and a C-arm connected to the frame. On end of the C-arm may be disposed with a radiation source 7021, and another end of the C-arm may be disposed with a flat panel detector 7022. The radiation source 7021 may be used to emit radiations, and the flat panel detector 7022 may be used to receive radiation passing through the patient on the catheter bed 701. The operation console 703 may be used to obtain a target position of the medical device. The processor 704 may be used to determine a target motion path of the medical device based on a current position and the target position of the medical device, and control the medical device to move from the current position to the target position along the target motion path.

Figure 8:
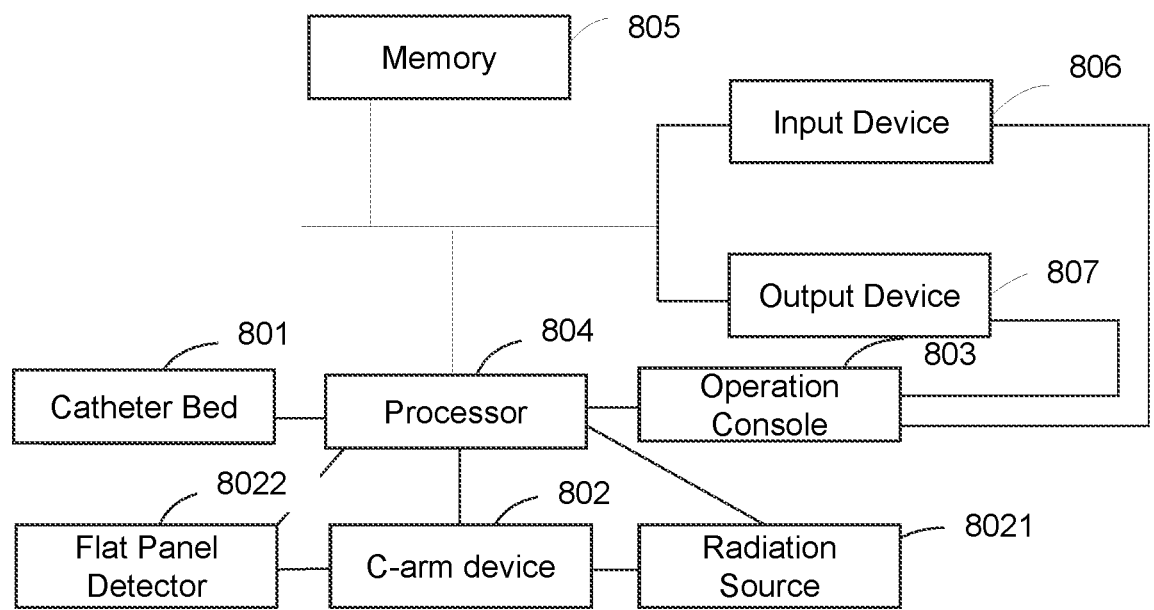
FIG. 8 is a structural block diagram illustrating a motion control system for a medical device according to some embodiments of the present disclosure.

In some embodiments, the radiation source 7021 and the flat panel detector 7022 on the C-arm may be oppositely disposed. The radiation source 7021 may be used to output radiations through the internal radiation source, and the flat panel detector 7022 may be used to receive the radiations after passing through the patient. As shown in FIG. 8, the operation console may further include an input device 806 and an output device 807, or a touch screen that simultaneously serves as an output device and an input device. The embodiment may use a touch screen as an example to explain the technical solution.

To facilitate obtaining the target position of the medical device, the embodiment may provide the user with a planning view of a current treatment room through a graphical user interface (GUI) of an operation console. Therefore, the user may directly input or select the target position in the planning view displayed by the GUI.

In some embodiments, the user may select the target position by clicking or double-clicking a desired position in the planning view.

In some embodiments, the user may input or select the target position by dragging or rotating a device icon representing the medical device in the planning view.

For example, the user may move the device icon from the current position to the target position by dragging in the planning view. As used herein, the current position may be a non-operation position, and the corresponding target position may be an operation position; or the current position may be an operation position, and the corresponding target position may be a non-operation position. The operation position may be a position where the user operates the medical device to perform a medical operation (e.g., a CT imaging), for example, a position adjacent to the catheter bed. The non-operating position may be a position where the medical device is not operated for any medical operation. For example, the position may be a position away from the catheter bed, the initial position of the medical device, a position away from the patient, etc.

As another example, the user may rotate the device icon (used to represent the position of the medical device) from the current position to the target position in the planning view. In some embodiments, the current position and the target position may be both operating positions, and the rotation operation is suitable for adjusting a scanning angle of the radiation source during a treatment process. In some embodiments, the current position and the target position may be both non-operating positions, and the rotation operation is suitable adjusting the radiation source for homing.

It may be understood that, in some embodiments, the drag of the device icon may correspond to a translation of the radiation source, and the rotation of the device icon may correspond to a rotation (e.g., change of the scanning angle) of the radiation source. In some embodiments, the drag of the device icon may correspond to a change in a translation of the flat panel detector, and the rotation of the device icon may correspond to a change in a scanning angle of the flat panel detector.

In some embodiments, the display screen of the console may be a touch screen. Therefore, the user may select the target position by dragging or rotating the device icon in the three-dimensional planning view. In some embodiments, the user may also select the target position in the planning view by clicking on the touch screen.

In some embodiments, the current location of the medical device may be obtained in real time by a position detection device of the medical device.

It should be understood that, the target motion path corresponding to a position adjustment of the medical device may be a path in a three-dimensional space. If the spatial arrangement of the treatment room changes frequently, a prohibited operation region may often change. To find a better or optimal target motion path, in the embodiment, while obtaining the target position of the medical device, the spatial image of the current space of the medical device may be obtained to determine a spatial distribution of the treatment room according to the spatial image, thereby determining the prohibited operation region.

The spatial image may be acquired by a camera installed in the medical device or the treatment room. The count of cameras may be one or more, as long as the spatial distribution of the possible motion path of the medical device may be obtained.

The target motion path of the medical device may be determined according to the current position, the target position, and the spatial image of the medical device. As used herein, the target motion path may be a fixed path or a dynamic path. The fixed path may be a determined full path that may not be adjusted during the operation of the medical device. The dynamic path may be a path optimized in real-time. The optimization of the dynamic path may be based on the real-time spatial image, and follow the anti-collision and the shortest path principle, so that the medical device may quickly move from the current position to the target position.

After the processor 704 determines the target motion path of the medical device, the medical device may be controlled to automatically move from the current position to the target position along the target motion path without the manual adjustment of a user, thereby simplifying the imaging operation process of the medical device.

As shown in FIG. 8, the motion control system may further include a memory 805. The count of processors 804 may be one or more. For brevity, one processor 804 may be taken as an example in FIG. 8. The processor 804, the memory 805, the input device 806, and the output device 807 in the medical device may be connected through a bus or other means. In FIG. 8, the connection through a bus may be used as an example. The catheter bed 801, the gantry 802, the operation console 803, the processor 804, the radiation source 8021, and the flat panel detector 8022 in FIG. 8 may be understood to be the same as the corresponding devices in FIG. 7.

The memory 805 may be a computer-readable storage medium that may be used to store software programs, computer-executable programs corresponding to the motion control process in the embodiments of the present disclosure. The processor 804 may execute various functional applications (e.g., implementing the above motion control process) and data processing of the motion control device by running software programs, instructions stored in the memory 805.

The memory 805 may mainly include a storage program region and a storage data region. The storage program region may store an operating system and application programs required for at least one function. The storage data region may store data created according to the use of the terminal, and the like. In addition, the memory 805 may include a high-speed random access memory, and may also include a non-volatile memory, such as at least one magnetic disk storage device, a flash memory device, or other non-volatile solid-state storage devices. In some embodiments, the memory 805 may further include memories remotely disposed with respect to the processor 804, and the remote memories may be connected to the device through a network. Examples of the above network may include but not be limited to the Internet, an intranet, a local area network, a mobile communication network, or the like, or any combinations thereof.

The input device 806 of the operation console 803 may be used to receive input numeric or character information, and generate signals related to user settings and function control of the motion control device.

The output device 807 of the operation console 803 may include a display device such as a display screen, for example, a display screen of a user terminal.

The embodiments of the present disclosure also provide a storage medium including computer-executable instructions, which are used to execute a motion control process when executed by a computer processor. The motion control process may include: obtaining a target position of the medical device, determining a target motion path of the medical device according to a current position and the target position of the medical device, and controlling the medical device to move from the current position to the target position along the target motion path.

After a medical device is moved to a target position, when a patient is loaded (e.g., lays or stands) on a catheter bed in the medical device for examination, the medical device may perform a registration recording process, which may record and store result information during a detection process or a treatment process. The result information may have a one-to-one correspondence with each patient, and may be viewed later.

In some embodiments, the medical device may automatically store the electronic information, generated during the treatment process, of the patient under a path of a current registration record. Therefore, in an actual process, if medical staff responsible for the registration record forget to close a registration record of a previous patient, the registration recording system of the medical device may automatically store the electronic information, generated in the treatment process, of the current patient under the name of the previous patient. If the medical staff closes the registration record of the previous patient and does not create a registration record of the current patient, the system may not store the electronic information generated by the current patient during the treatment process, and the information may be lost. If the medical staff suddenly finds that there is no registration record created for the current patient and immediately creates a new registration record for the current patient, the registration recording system may only store the electronic information obtained under the path of the registration record after the registration record is created. However, the electronic information before the registration record is created may be lost. It should be understood that no matter which of the above situations occurs, it may be inconvenient for medical record management. Therefore, in some embodiments of the present application, an accurate information registration control process may be provided.

Figure 9:
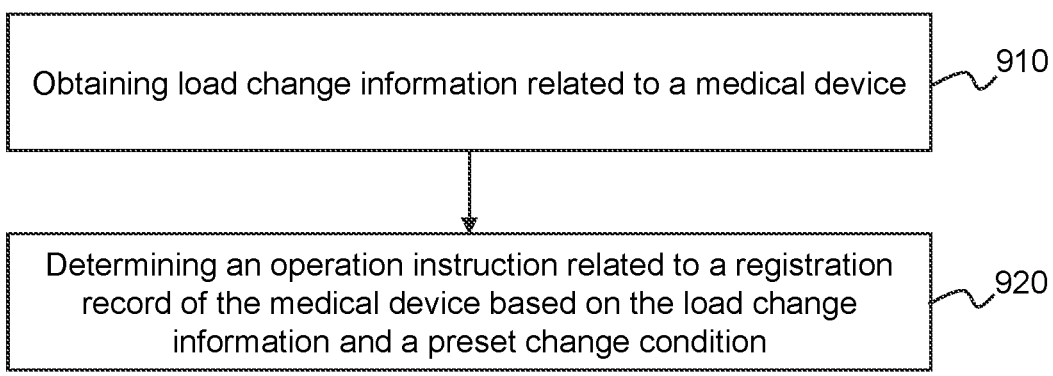
FIG. 9 is a flowchart illustrating an information registration control process according to some embodiments of the present disclosure.
Figure 11A:
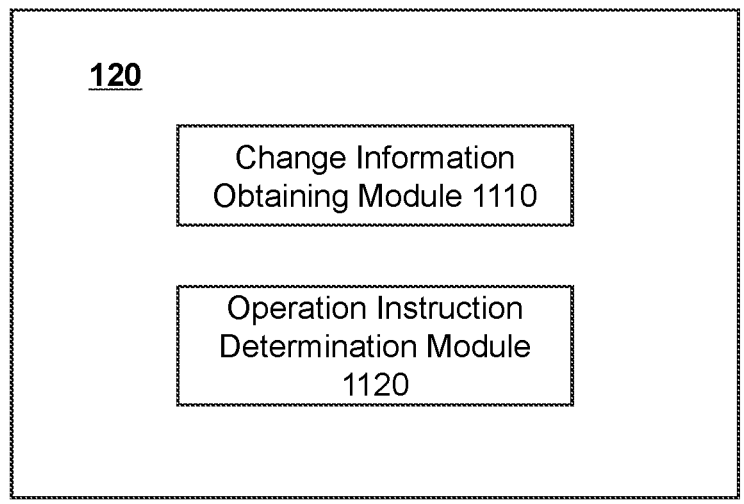
FIG. 11A is a structural block diagram illustrating an information registration control device according to some embodiments of the present disclosure.
Figure 11B:
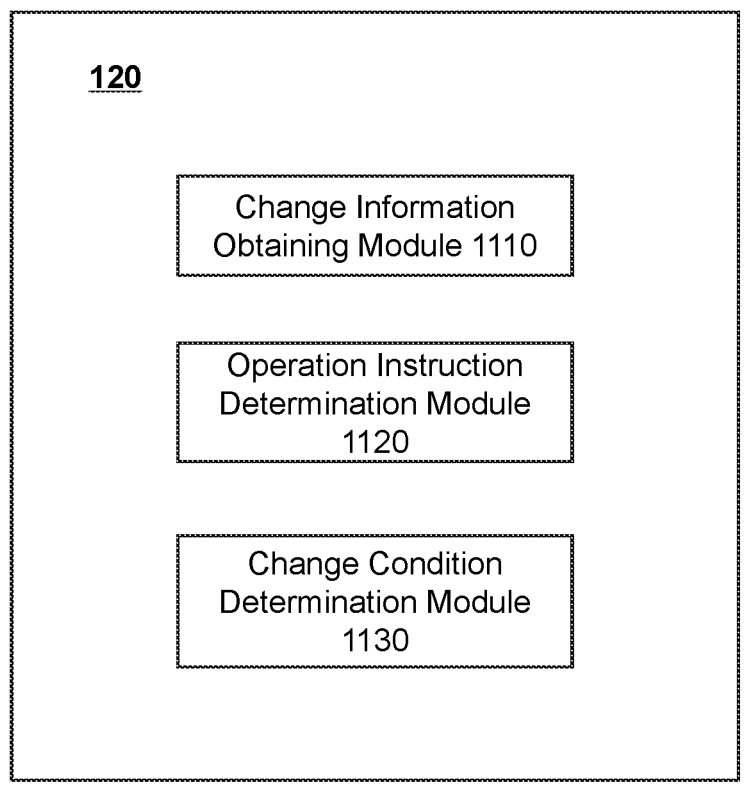
FIG. 11B is a structural block diagram illustrating an information registration control device according to some embodiments of the present disclosure.

FIG. 9 is a flowchart illustrating an information registration control process according to some embodiments of the present disclosure. The technical solution of the embodiments may be applicable to the case where information registration records are controlled according to a change of a load that a bed of a medical device bears. The process 900 may be executed by an information registration control device according to the embodiment of the present disclosure. The information registration control device may be implemented in software or hardware, e.g., the processing device 120. With reference to FIGS. 9, 11A, and 11B, the process 900 may include one or more of the following operations.

In 910, the processing device 120 may obtain load change information related to the medical device. The load change information may indicate the change of related parameters of the bed generated by loading or unloading a patient. In some embodiments, the related parameters of the bed may include the pressure or mass to which the bed is subjected. Correspondingly, in some embodiments, the load change information may include pressure change information or mass change information.

In 920, the processing device 120 may determine an operation instruction related to the registration record of the medical device based on the load change information and a preset change condition. In some embodiments, the operation instruction related to the registration record of the medical device may be understood as a command instructing the medical device to perform an operation related to the registration record of the medical device, for example, an operation instruction for closing a registration record of an unloaded patient, an operation instruction that pops up a registration record to be entered, etc. In some embodiments, the medical staff may close the registration record of the unloaded patient or pop up a new registration record to be entered based on the operation instruction.

In some embodiments, the operation instruction may be displayed on a display, or remind a user through a sound playing module. In some embodiments, after a display screen of the medical device displays the operation instruction to close the registration record of the unloaded patient, the medical staff may close the registration record of the unloaded patient through a mouse or a touch screen to execute the operation instruction. In some embodiments, the medical device may automatically execute the operation instruction. For example, when the pressure change information indicates that a patient is unloaded from the bed, the medical device may automatically close the registration record of the unloaded patient, or when the pressure change information indicates that a new patient is loaded on the bed, the medical device may pop up the registration record of the new patient, so that the medical staff may perform an information registration for the new patient. For another example, when the mass change information indicates that a patient is unloaded from the bed, the medical device may close the registration record of the unloaded patient, or when the mass change information indicates that a new patient is loaded on the bed, the medical device may pop up the registration record of the new patient, so that the medical staff may perform the information registration for the new patient.

Figure 10:
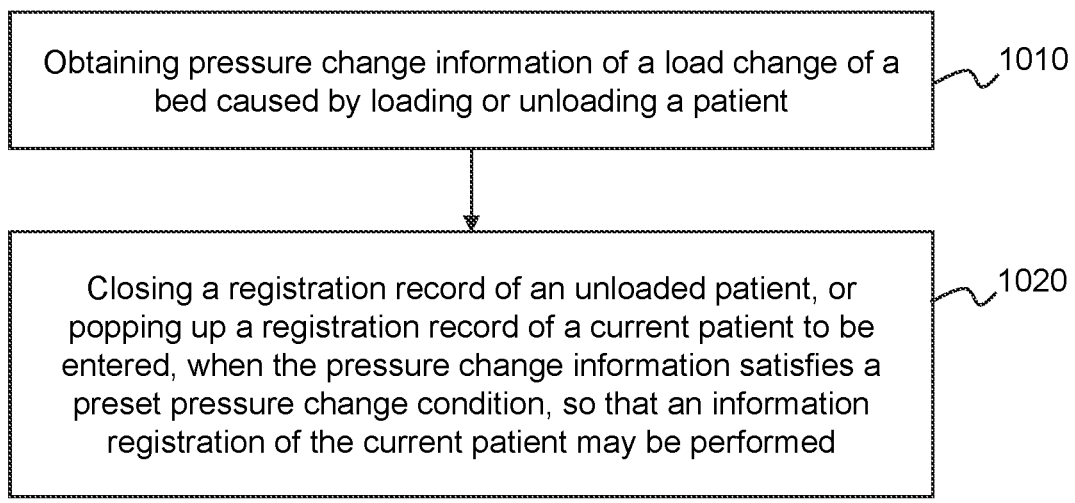
FIG. 10 is a flowchart illustrating an information registration control process based on changes in pressure information according to some embodiments of the present disclosure.

FIG. 10 is a flowchart illustrating an information registration control process based on pressure change information according to some embodiments of the present disclosure.

In 1010, the processing device 120 may obtain the pressure change information of a load change of a bed caused by loading or unloading a patient. The loading a patient may refer to the process that a patient lies on or stands on a bed, and the unloading a patient may refer to the process that a patient leaves the bed.

To facilitate the management of the treatment process, each treatment project (e.g., an imaging project, a surgery project, a surgery and treatment project, etc. of the patient on the bed) of the patient may need to correspond to a registration record.

For the treatment project that requires the bed, the weight of the patient may be applied to the bed when the patient is lying on the bed, resulting in a large change in the loading pressure on the bed. Thus, the processing device 120 may control the registration record of the patient based on the pressure change information of the load on the bed. To control the registration record of the patient based on the pressure change information of the load on the bed, it may be necessary to obtain the pressure information, detected by a pressure detection device, on the bed in real time. For example, the pressure change information may refer to real-time pressure changes, such as from the real-time pressure value of A to the real-time pressure value A+700 N (an approximate gravity corresponding to a bodyweight of 70 kg), or from the real-time pressure value A+700 N to the real-time pressure value A.

In 1020, when the pressure change information satisfies a preset pressure change condition, the processing device 120 may close the registration record of the unloaded patient, or pop up the registration record of the current patient so that the medical staff may perform the information registration for the current patient.

In some embodiments, the pressure change information may include a preset positive pressure change condition and/or a preset negative pressure change condition. A positive pressure change may correspond to a pressure increase caused by loading the patient, and a negative pressure change may correspond to a pressure decrease caused by unloading the patient.

The preset positive pressure change condition may refer to that the pressure applied to the bed caused by loading the patient exceeds a preset positive threshold. If the pressure change information satisfies the preset positive pressure change condition, it may refer to that the patient is currently lying on bed for treatment. At this time, the registration record to be entered may be automatically popped up, or an instruction message (e.g., a pop-up, a voice broadcast, etc.) prompting the registration record to be entered may be generated, to remind the medical staff to complete the information registration of the current patient as soon as possible. The positive threshold may be a pressure threshold preset by the medical staff, for example, 0-300 N. For example, the positive threshold may be 50 N, 100 N, 150 N, 200 N, 250 N, 300 N, or any other suitable value. The medical staff may habitually look at an operation console or an information display screen before starting treatment. Therefore, when finding that the information registration of the current patient is not yet entered, the medical staff may complete the information registration of the current patient before starting the treatment of the patient, which may prevent the medical staff from carrying out the treatment for the current patient when the patient has not been registered, and may ensure that electronic information generated by each device during the treatment of the current patient may be stored in the name of the current patient in time.

In some embodiments, when it is detected that the pressure change information on the bed satisfies the preset positive pressure change condition, the processing device 120 may automatically detect whether the registration record of the unloaded patient is closed. If the registration record of the unloaded patient is not closed, the processing device 120 may close the registration record of the unloaded patient, and a registration record to be entered for the current patient may be popped up to remind the medical staff to complete the information registration of current patient as soon as possible.

The preset negative pressure change condition may refer to that a pressure drop value of the bed caused by unloading the patient exceeds a preset negative threshold. If the pressure change information satisfies the preset negative pressure change condition, it may refer to that the patient has finished the treatment and is leaving the bed. The negative threshold may be a pressure threshold preset by the medical staff, for example, 0-300 N. For example, the negative threshold may be may be 50 N, 100 N, 150 N, 200 N, 250 N, 300 N, or any other suitable value. In some embodiments, the value of the negative threshold may be the same as or different from the value of the positive threshold. It may be understood that after the patient finishes the treatment, the treatment device(s) may no longer generate any electronic information that needs to be stored in the name of the patient. In addition, if the registration record remains open, it may also affect the storage of electronic information of subsequent patients. Therefore, in some embodiments, when it is detected that the pressure change information satisfies the preset negative pressure change condition, the registration record of the unloaded patient may be automatically closed.

In some embodiments, the preset pressure change condition may include that a pressure change of the bed is within a range. For example, the range may from −B to B. B may be set arbitrarily. As another example, the range may from −C to B. C may be set arbitrarily and different from B. In some embodiments, the preset pressure change condition may also be set according to a weight range of the patient. For example, a corresponding preset pressure change condition may be set according to weights of a certain count of patients. In some embodiments, the preset pressure change condition may be preset. In some embodiments, the preset pressure change conditions may also be automatically adjusted according to specific conditions. For example, the medical device may first obtain weight information of a patient, and then determine the preset positive pressure change condition according to the weight information of the patient. In this regard, each patient may correspond to a certain preset positive pressure change condition. For another example, the medical device may first obtain the weight information of a patient, and then determine the preset negative pressure change condition according to the weight information of the patient. In this regard, each patient may correspond to a certain preset negative pressure change condition. In some embodiments, a weight scale for obtaining the weight information of the patient may be disposed on one side of the bed, so as to obtain the weight information of the patient before the patient lies on the bed.

It may be understood that for the image detection project (e.g., CT, X-ray, PET, MRI, etc.), the patient may be firstly positioned and then performed imaging. The patient may need to repeatedly adjust the position according to the instructions of the medical staff during the positioning process. For some people, it may be possible to adjust the pose without leaving the bed. However, for children or critically ill patients, it may be necessary to them to leave the bed and adjust their poses. For example, the medical staff may need to hold a child up and then put the child in a suitable position. In some embodiments, the medical staff may need to hold a child up and put the child down again. Therefore, although the pressure change information of the load on the bed appears multiple positive and negative changes, all of the changes may occur in the preparation stage of the treatment of the same patient. Hence, in the embodiment, before closing the registration record of the unloaded patient, it may be first determined whether a time interval between the unloaded patient and the loading patient exceeds a preset time threshold. If the time interval does not exceed the preset time threshold, the registration record may be kept open. If the time interval exceeds the preset time threshold, the patient may be deemed to be finishing the treatment, and the registration record of the unloaded patient may be closed at this time. In some embodiments, the preset pressure change condition may include the preset negative pressure change condition. Before closing the registration record of the unloaded patient, it may be first determined whether the pressure change information satisfies the preset negative pressure change condition. If the pressure change information satisfies the preset negative pressure change condition, and then, a time interval may be counted starting from the time when the preset negative pressure change condition is satisfied until the bed is loaded again to satisfy the preset positive pressure condition. It may be determined whether the time interval exceeds the preset time threshold. If the time interval does not exceed the preset time threshold, the registration record of the unloaded patient may not be closed, or the registration record to be entered may not be popped up. If the time interval exceeds the preset time threshold, the registration record may be closed and the registration record to be entered may be popped up.

Figure 12A:
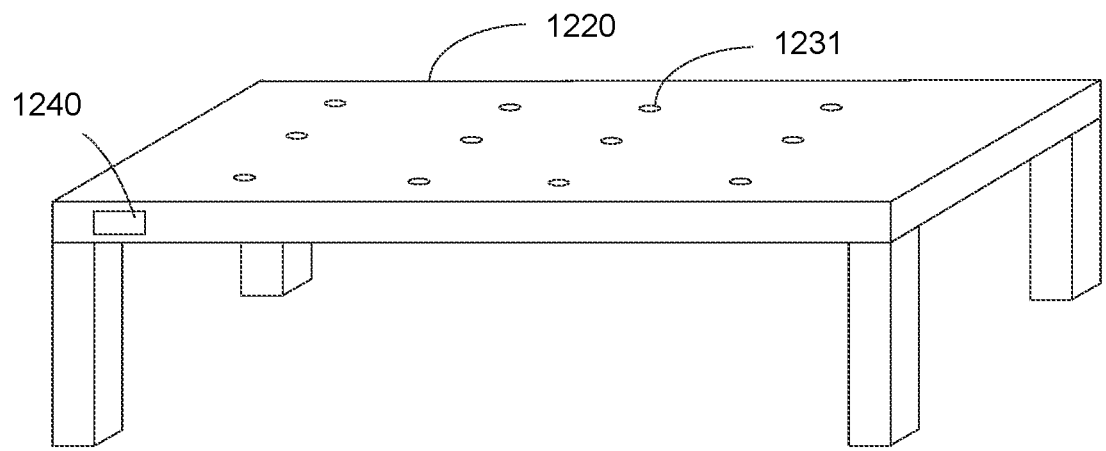
FIG. 12A is a schematic diagram illustrating an exemplary information registration control system according to some embodiments of the present disclosure.
Figure 12B:
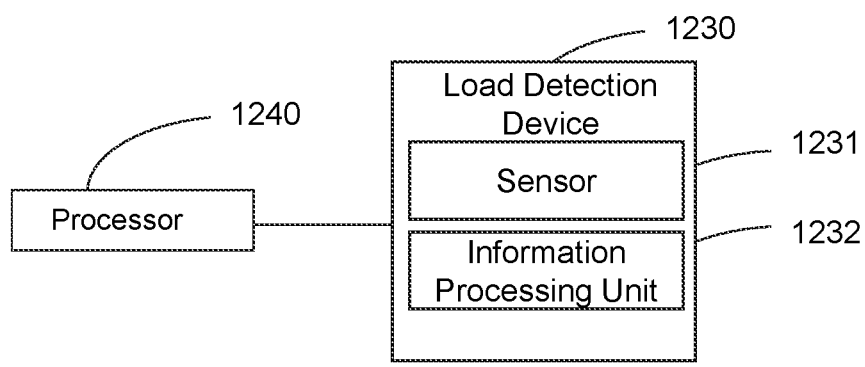
FIG. 12B is a structural block diagram illustrating an exemplary information registration control system according to some embodiments of the present disclosure.

To better detect the pressure change information applied by the patient to the bed, the pressure detection device may include a sensor 1231 and an information processing unit 1232. The sensor 1231 may be preferably distributed on the bed 1220 in the form of an array. The information processing unit 1232 may be used to determine the pressure change information corresponding to the current load of the bed according to the pressure information output by each sensor, as shown in FIG. 12A and FIG. 12B.

To facilitate the medical staff to check the state of the registration record, different states of the registration records may be displayed with different mark information. For example, the mark information may include colors. The color of the registration record to be entered may be yellow, and the color of the complete registration record (e.g., the registration record of the unloaded patient) may be green. To facilitate the medical staff to check the state of the registration record, the registration record may be displayed on the display screen of the operation console associated with the bed in real time.

The technical solution of the information registration control process according to the embodiment of the present disclosure may include obtaining the pressure change information generated by the load change of the bed caused by loading or unloading the patient. When the pressure change information satisfies the preset pressure change condition, the information registration control process may include closing the registration record of the unloaded patient or popping up the registration record to be entered for the current patient so that the medical staff may perform the information registration of the current patient. If the pressure change information on the bed indicates that a patient is lying on the bed to receive the treatment, a registration record to be entered may be popped up to enable the medical staff to complete the information registration of the current patient in time. If the pressure change information on the bed indicates that the patient has left the bed, the registration record of the unloaded patient may be closed. The information registration control process may achieve that the registration record may be closed in time when the patient leaves the bed to prevent the electronic information of the next patient generated during the treatment process from being stored under the name of the previous patient, and the registration record to be entered may be popped up in time, when a new patient is lying on the bed, to remind the medical staff to complete the information registration for the new patient. Therefore, the electronic information generated during the treatment process may be stored in the name of the right patient, thereby helping to improve the effectiveness and efficiency of the patient treatment information management.

In some embodiments of the present disclosure, the technical solution of the registration control process may further include obtaining the mass change information generated by the load change of the bed caused by loading or unloading the patient. When the mass change information satisfies a preset mass change condition, the registration control process may include closing the registration record of the unloaded patient, or popping up the registration record to be entered for the current patient so that medical staff may perform the information registration for the current patient. The specific process of performing the registration control based on the mass change information may be performed with reference to the above-mentioned process of performing the registration control based on the pressure change information, which is not repeated herein. However, a change may need to be made by replacing the pressure sensor with a mass detection device to detect the mass change on the bed.

FIG. 11A is a structural block diagram illustrating an information registration control device according to some embodiments of the present disclosure. The device is used to execute the information registration control process provided by any of the above embodiments. The information registration control device may be implemented by software or hardware. The information registration control device may include: a change information obtaining module 1110 and an operation instruction determination module 1120.

The change information obtaining module 1110 may obtain load change information related to the medical device. The load change information may be pressure change information or mass change information generated by a load change of the bed caused by loading or unloading the patient.

The operation instruction determination module 1120 may determine an operation instruction related to a registration record of the medical device based on the load change information and a preset change condition. For example, when the pressure change information satisfies a preset pressure change condition, the operation instruction determination module 1120 may close the registration record of an unloaded patient, or pop up the registration record of a current patient so that the medical staff may perform an information registration. For another example, when the mass change information satisfies a preset mass change condition, the operation instruction determination module 1120 may close the registration record of the unloaded patient, or pop up the registration record of the current patient so that the medical staff may perform the information registration.

In some embodiments, the operation instruction determination module 1120 may pop up the registration record to be entered for the current patient when the preset pressure change condition satisfies the preset positive pressure change condition.

In some embodiments, the operation instruction determination module 1120 may directly pop up the registration record of the current patient, or close the registration record of the previously unloaded patient and pop up the registration record of the current patient.

In some embodiments, the operation instruction determination module 1120 may first determine whether the preset negative pressure change condition is satisfied before closing the registration record of the unloaded patient. If the pressure change information satisfies the preset negative pressure change condition, a time interval may be counted starting from the time when the preset negative pressure change condition is satisfied until the bed is loaded again to satisfy the preset positive pressure condition. It may be determined whether the time interval exceeds a preset time threshold. If the time interval does not exceed the preset time, the registration record of the unloaded patient may not be closed, or the registration record to be entered may not be popped up. If the time interval exceeds the preset time threshold, the registration record may be closed and the registration record to be entered may be popped up.

In some embodiments, the operation instruction determination module 1120 may close the registration record of the unloaded patient when the pressure change information satisfies the preset negative pressure change condition.

In some embodiments, the change information obtaining module 1110 may obtain weight information of the patient. Correspondingly, the information registration control device may further include a change condition determination module 1130 (referring to FIG. 11B). The change condition determination module 1130 may obtain the weight information of the patient and determine the preset pressure change condition according to the weight information.

The technical solution of the information registration control process according to the embodiment of the present disclosure may include obtaining the pressure change information generated by the load change of the bed caused by loading or unloading the patient. When the pressure change information satisfies the preset pressure change condition, the information registration control process may include closing the registration record of the unloaded patient, or popping up the registration record to be entered for the current patient so that the medical staff may perform the information registration of the current patient. If the pressure change information on the bed indicates that a patient is on the bed to receive the treatment, a registration record may be popped up to enable the medical staff to complete the information registration of the current patient in time. If the pressure change information on the bed indicates that the patient has left the bed, the registration record of the unloaded patient may be closed.

The information registration control process may achieve that the registration record may be closed in time when the patient leaves the bed to prevent the electronic information of the next patient generated during the treatment process from being stored under the name of the previous patient, and the registration record to be entered may be popped up in time, when the current patient is lying on bed, to remind the medical staff to complete the information registration of the current patient. Therefore, the electronic information generated during the treatment process may be stored in the name of the right patient, thereby helping to improve the effectiveness and efficiency of the patient treatment information management.

The information registration control device provided by the embodiments of the present disclosure may execute the information registration control process provided by any embodiment of the present disclosure, and have the corresponding functions and beneficial effects of the execution process.

FIG. 12A and FIG. 12B are information registration control systems according to some embodiments of the present disclosure. As shown in FIGS. 12A and 12B, the information registration control system may include a bed 1220, a load detection device 1230, and a processor 1240. The bed 1220 may be used to carry a patient. The bed 1220 may be the same as or similar to the catheter bed 701 in FIG. 7. The load detection device 1230 may be used to detect load change information of the bed 1220. In some embodiments, the load detection device 1230 may include a pressure sensor, a mass sensor, or the like. The processor 1240 may be disposed on the bed 1220 or other components. In some embodiments, the processor 1240 may be used to receive the load change information of the bed 1220 detected by the load detection device 1230. When the load change information satisfies a preset load change conditions, the processor 1240 may close a registration record of an unloaded patient, or pop up a registration record of a current patient so that medical staff may perform the information registration of the current patient. In some embodiments, the bed may be a portion of a medical device. The medical device may include a digital subtraction angiography system, a C-arm device, an X-ray system, or the like, or any combination thereof.

The pressure change information may be taken as a specific example. For the treatment project that requires the bed, the weight of the patient may be applied to the bed when the patient is lying on the bed, resulting in a large change in the loading pressure on the bed. Thus, the processor may control the registration record of the patient based on the pressure change information of the load on the bed. To control the registration record of the patient based on the pressure change information of the load on the bed, it may be necessary to obtain the pressure information, detected by a pressure detection device, on the bed in real time. For example, the pressure change information may refer to real-time pressure changes, such as from the real-time pressure value of A to the real-time pressure value A+700 N (an approximate gravity corresponding to a body-weight of 70 kg), or from the real-time pressure value A+700 N to the real-time pressure value A.

In some embodiments, the pressure change information may include a preset positive pressure change condition and/or a preset negative pressure change condition. A positive pressure change may correspond to a pressure increase caused by loading the patient, and a negative pressure change may correspond to a pressure decrease caused by unloading the patient.

The preset positive pressure change condition may refer to that the pressure applied to the bed caused by loading the patient exceeds a preset positive threshold. If the pressure change information satisfies the preset positive pressure change condition, it may refer to that the patient is currently lying to bed for treatment. At this time, the registration record to be entered may be automatically popped up, or an instruction message (e.g., a pop-up, a voice broadcast, etc.) prompting the registration record to be entered may be generated, to remind the medical staff to complete the information registration of the current patient as soon as possible. The medical staff may habitually look at an operation console or an information display screen before starting treatment. Therefore, when finding that the information registration of the current patient is not yet entered, the medical staff may complete the information registration of the current patient before starting the treatment of the patient, which may prevent the medical staff from carrying out the treatment for the current patient when the patient has not been registered, and may ensure that electronic information generated by each device during the treatment of the current patient may be stored in the name of the current patient in time.

In some embodiments, when it is detected that the pressure change information on the bed satisfies the preset positive pressure change condition, the processor may automatically detect whether the registration record of the unloaded patient is closed. If the registration record of the unloaded patient is not closed, the processor may close the registration record of the unloaded patient, and a registration record to be entered for the current patient may be popped up to remind the medical staff to complete the information registration of current patient as soon as possible.

The preset negative pressure change condition may refer to that a pressure drop value of the bed caused by unloading the patient exceeds a preset negative threshold. If the pressure change information satisfies the preset negative pressure change condition, it may refer to that the patient has finished the treatment and is leaving the bed. It may be understood that after the patient finishes the treatment, the treatment device(s) may no longer generate any electronic information that needs to be stored in the name of the patient. In addition, if the registration record remains open, it may also affect the storage of electronic information of subsequent patients. Therefore, in some embodiments, when it is detected that the pressure change information satisfies the preset negative pressure change condition, the registration record of the unloaded patient may be automatically closed.

To facilitate the medical staff to check the state of the registration record, different states of the registration records may be displayed with different mark information. For example, the mark information may include colors. The color of the registration record to be entered may be yellow, and the color of the complete registration record (e.g., the registration record of the unloaded patient). To facilitate the medical staff to check the state of the registration record, the registration record may be displayed on the display screen of the operation console associated with the bed in real-time.

The bed provided by some embodiments of the present disclosure and the information registration control process provided by the above embodiments may belong to the same inventive concept. Technical details not described in detail in the embodiment of the present disclosure may refer to the above embodiments. The embodiment of the present disclosure may have the same beneficial effects as the above embodiments.

Figure 13:
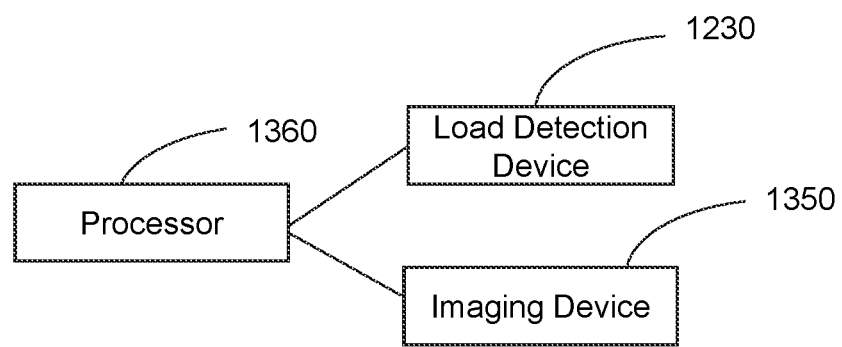
FIG. 13 is a structural block diagram illustrating an exemplary medical device according to some embodiments of the present disclosure.

FIG. 13 is an exemplary medical device according to some embodiments of the present disclosure. The medical device may include a C-arm device. In some embodiments, the C-arm device may include an angiography machine. Although the medical device is described by taking the C-arm device as an example herein, the medical device may be a computer tomography device, a nuclear magnetic resonance imaging device, a digital X-ray photography device, a positron emission tomography device, a single-photon emission computer tomography scanning device, a dual-mode scanning device, or the like.

As shown in FIGS. 12A, 12B, and 13, the medical device may include a bed 1220, a load detection device 1230, an imaging device 1350, and a processor 1360. The bed 1220 may be used to carry a patient. The load detection device 1230 may be used to detect load change information of the bed caused by the bed 1220 loading or unloading the patient. The imaging device 1350 may be disposed on one side of the bed 1220 to obtain a medical image of a patient according to an obtaining signal. The processor 1360 may be used to receive the load change information of the bed detected by the load detection device 1230. When the load change information satisfies a preset load change condition, the processor 1360 may close a registration record of an unloaded patient, or pops up a registration record to be entered for a new patient so that medical staff may perform an information registration for the new patient. The processor 1360 may further control the imaging device to obtain the medical image of the current patient when the obtaining signal is detected.

To better detect the pressure change information applied by the patient to the bed, the pressure detection device may include a sensor 1231 and an information processing unit 1232. The sensor 1231 may be distributed on the bed 1220 in the form of an array. The information processing unit 1232 may be used to determine the pressure change information corresponding to the current load of the bed according to the pressure information output by each sensor, as shown in FIG. 12A and FIG. 12B.

In the technical solution according to the embodiment of the present disclosure, if the pressure change information on the bed indicates that a patient is on the bed to receive the treatment, a registration record may be popped up to enable the medical staff to complete the information registration for the current patient in time. If the pressure change information on the bed indicates that the patient has left the bed, the registration record of the unloaded patient may be closed. The medical device may achieve that the registration record may be closed in time when the patient leaves the bed to prevent the electronic information of the next patient generated during the treatment process from being stored under the name of the previous patient. The registration record to be entered may be popped up in time, when the current patient is lying on bed, to remind the medical staff to complete the information registration for the current patient.

Therefore, the electronic information generated by the patient during the treatment process may be stored in the name of the right patient, thereby helping to improve the effectiveness and efficiency of the patient treatment information management.

Figure 14:
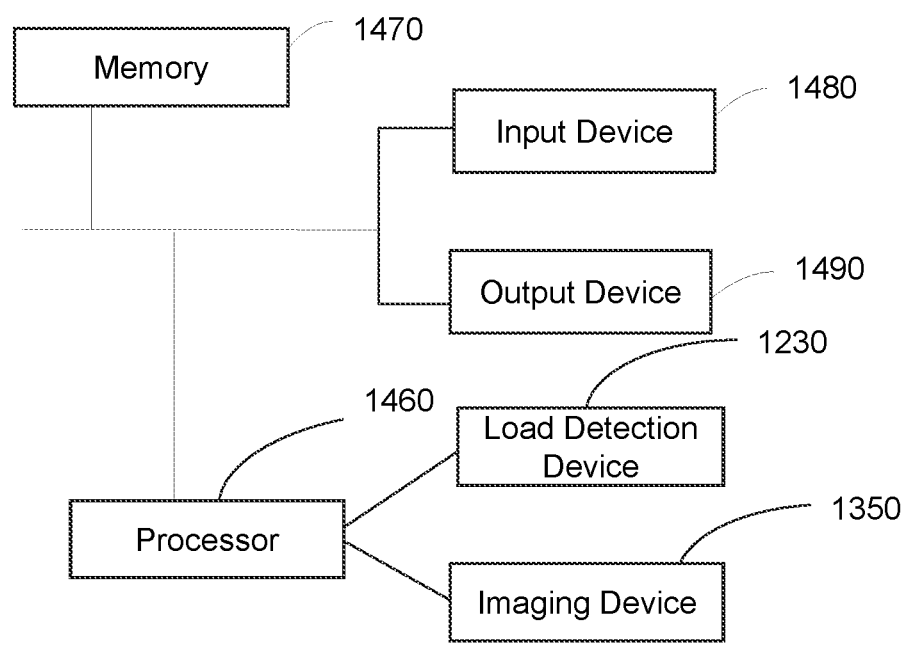
FIG. 14 is a structural block diagram illustrating an exemplary medical device according to some embodiments of the present disclosure.

The medical device may further include a memory 1470, an input device 1480, and an output device 1490. The count of processors 1460 may be one or more. In FIG. 14, one processor may be used as an example. The memory 1470, the input device 1480, and the output device 1490 may be connected by a bus or other means. In FIG. 14, a bus may be used as an example for connection.

The memory 1470 may be a computer-readable storage medium that may be used to store software programs, computer-executable programs corresponding to the information registration control process in the embodiment of the present disclosure. The processor 1460 may execute software functions, and instructions, stored in the memory 1470 to execute various functional applications and data processing to implement the above-mentioned information registration control process.

The memory 1470 may include a storage program region and a storage data region. The storage program region may store an operating system and application programs required for at least one function. The storage data region may store data created according to the use of the terminal, etc. In addition, the memory 1470 may include a high-speed random access memory, or a non-volatile memory, such as at least one magnetic disk storage device, a flash memory device, or other non-volatile solid-state storage devices. In some embodiments, the memory 1470 may further include memories remotely disposed with respect to the processor 1460, and the remote memories may be connected to the medical device through a network. Examples of the above network may include but not be limited to the Internet, an intranet, a local area network, a mobile communication network, or the like, or any combinations thereof.

The input device 1480 may be used to receive input numeric or character information, and generate signals related to user settings and the function control of the medical device. In some embodiments, the input device 1480 may be the same as the input device 806 in FIG. 8.

The output device 1490 may include a display device such as a display screen, for example, a display screen of a user terminal. In some embodiments, the output device 1490 may be the same as the output device 807 in FIG. 8.

The embodiments of the present disclosure further provide a storage medium containing computer-executable instructions, which, when executed by a computer processor, are used to execute an information registration control process. The information registration control process may include: obtaining load change information related to a medical device; and determining an operation instruction related to a registration record of the medical device based on the load change information and a preset change condition. In some embodiments, if the load change information satisfies the preset change condition, it is determined that the operation instruction is to close a registered registration record (e.g., the registration record of an unloaded patient) and/or pop up a registration record to be entered (e.g., the registration record of a current patient). The load change information may include pressure change information or mass change information.

In some embodiments, when the load change information includes the pressure change information, the method may further include: obtaining the pressure change information generated by a load change of a bed caused by loading or unloading a patient; when the pressure change information satisfies the preset pressure change condition, closing a registration record of an unloaded patient, or popping up a registration record of a current patient so that medical staff may perform an information registration for the current patient.

For better observation, the medical device may further include a display for displaying the motion position described in connection with FIGS. 4 and 5, e.g., a position away from the target position, and/or a deviation from the target position. The display may also be used for displaying a registration record described in connection with FIG. 9, e.g., which patient the current registration record belongs to and/or whether the registration record of the next patient is opened or popped up. In some embodiments, a medical device capable of displaying related parameter information related to the medical device system is provided. As used herein, the relevant parameters may include parameter configuration information and/or operation parameter information of the medical device. In some embodiments, the display may be used to display motion parameters of related devices. For example, the display may display collision information of a C-arm device, which may reduce the collision probability of the C-arm when an operator operates the C-arm device. As another example, in the motion control scene of the C-arm device described above, a current motion path and collision information of the C-arm device may also be displayed to reduce the occurrence of abnormal events during the automatic motion.

In some embodiments, the display of the medical device may be disposed opposite a bed, which is not convenient for observation. Taking the C-arm device as an example, a doctor may need to repeatedly observe the motion of the monitor and the gantry of the C-arm device when moving the C-arm, which is not convenient for the doctor. Therefore, the doctor may spend much time in adjusting an angle of the C-arm. In addition, adjustment accuracy may be seriously affected by human factors. Therefore, in some embodiments of the present disclosure, a device capable to display angle information of the C-arm and the C-arm gantry on the C-arm side may be provided.

Figure 15:
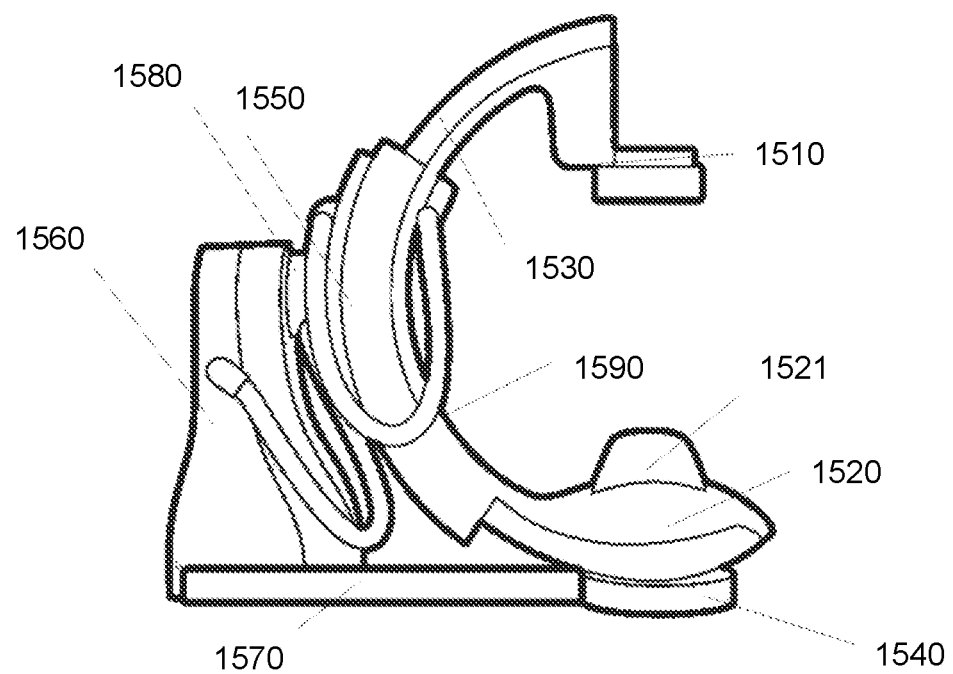
FIG. 15 is a schematic structural diagram of an exemplary medical device according to some embodiments of the present disclosure.

FIG. 15 is a schematic structural diagram illustrating an exemplary medical device according to some embodiments of the present disclosure. The medical device may include a C-arm device. In some embodiments, the C-arm device may include an angiography machine. Although the medical device is described by taking the C-arm device as an example herein, the medical device may be a computer tomography device, a nuclear magnetic resonance imaging device, a digital X-ray photography device, a positron emission tomography device, a single-photon emission computer tomography scanning device, a dual-mode scanning device, or the like. As shown in FIG. 15, the C-arm device may include: a detector 1510 (e.g., the flat panel detector described above), a radiation source 1520, a collimator 1521, a C-arm 1530, a rotating column 1540, a C-arm slide rail 1550, a support arm 1560, a base 1570, a connection portion 1580, and a display 1590. As used herein, the C-arm 1530 may be disposed and moved in the C-arm rail 1550. The detector 1510 may be disposed at one end of the C-arm 1530. The radiation source 1520 may be disposed at another end of the C-arm 1530, which is opposite to the detector 1510. One end of the base 1570 may be connected to the support arm 1560. The display 1590 may be used to display parameter configuration information and/or operation parameter information related to the C-arm device.

In some embodiments, the parameter configuration information may refer to parameter information used to configure the C-arm device. The parameter configuration information may be set when the medical device is produced, or when the medical device is used. In some embodiments, the parameter configuration information may include time information, device information, patient information, or the like, or any combination thereof. The time information may refer to the time of the medical device. In some embodiments, the time information may be manually set by a user, or automatically updated by connecting to the network. The device information may include information such as a power of the radiation source, performance parameters of each component, operating duration of the medical device, or the like, or any combination thereof. In some embodiments, the device information may be manually set by the user, or automatically updated by the medical device according to usage loss. The patient information may include age, sex, weight, a position to be examined, a historical detection record, etc. of the patient. In some embodiments, the patient information may be set during the registration record control process above.

In some embodiments, the operation parameter information may refer to parameter information that may change during the operation of the C-arm device. In some embodiments, the operation parameter information may include angle information of the C-arm 1530, height information of a bed surface, collision information, a distance (SID) between the radiation source 1520 and an imaging surface of the detector 110, status information of the medical device, image (e.g., a reconstructed image) Information, or the like, or any combination thereof. The collision information may refer to information related to a collision. In some embodiments, the collision information may include information about an impending collision, information about an already occurred collision, and so on. The information about the impending collision may indicate that a distance between a part of the medical device and other objects (e.g., an obstacle, an object to be collided, other parts of the medical device, etc.) is too small, which needs attention of an operator. The information about the impending collision may include the part of the medical device about to collide, distance information between the medical device and other objects, or the like. The information about the already occurred collision may include a position of the collision on the medical device, pressure generated by the collision, or the like. The status information of the medical device may include current operation conditions and/or parameters of the medical device or a portion thereof, for example, whether the medical device or a portion thereof is operating normally, whether storage space is full, power information of part of the medical device that uses batteries. The image information may refer to inherent information of an image generated by the medical device, for example, the format of the image, the time when the image is generated, the device used to generate the image, the user who generated the image, or the like, or any combination thereof. In some embodiments, the image information may be automatically generated by the medical device when generating an image.

The angle information of the C-arm 1530 may be rotation information that reflects the change of the rotation angle of the C-arm 1530. The angle or rotation angle of the C-arm 1530 may be initially set to 0 degrees so that the angle information of the C-arm 1530 may be determined at various time points.

In the technical solution of the embodiment of the present disclosure, by adding the display 1590 on the C-arm side of the C-arm device, the information such as the angle information of the C-arm 1530, the height information of the bed surface, the collision information, the distance (SID) between the radiation source 1520 and the imaging surface of the detector 1510 may be displayed, which may solve the problem that the display disposed on the C-arm device is not convenient, and improve the accuracy of the C-arm motion and the safety of the detection process.

In some embodiments, the C-arm device may include a C-arm. The detector may be disposed at one end of the C-arm, and the radiation source may be disposed at another end of the C-arm, which is opposite to the detector. Correspondingly, the display 1590 may be disposed at any position of the C-arm 1530.

In some embodiments, the C-arm device may further include a C-arm slide rail 1550. The C-arm 1530 may be moved along the C-arm slide rail 1550, and thus the positions of the detector and the radiation source may be adjusted. Correspondingly, the display 1590 may be disposed at any position of the C-arm slide rail 1550 (e.g., at the middle position of the C-arm slide rail 1550 shown in FIG. 15).

In some embodiments, the C-arm device may further include a support arm 1560 and a connection portion 1580. The support arm 1560 may be used to provide support for the C-arm, and the connection portion 1580 may be located between the support arm 1560 and the C-arm slide rail 1550 for connecting the C-arm slide rail 1550 and the support arm 1560. Correspondingly, the display 1590 may be disposed at any position of the support arm 1560 and the connection portion 1580 (e.g., at the center of the connection portion 1580).

In some embodiments, the C-arm device may further include a base 1570. The base 1570 may be used to fix the support arm 1560 and stabilize the C-arm device. In some embodiments, the support arm 1560 and the base 1570 may be regarded as a whole, and the functions of the support arm 1560 and the base 1570 may be equivalent to the gantry in FIG. 7. In some embodiments, if the C-arm device includes the slide rail 1550, the support arm 1560, the base 1570, and the connection portion 1580, the slide rail 1550, the support arm 1560, the base 1570, and the connection portion 1580 may be regarded as a whole, and the functions of the support arm 1560, the base 1570, and the base 1570 may be equivalent to the gantry in FIG. 7.

In some embodiments, a working surface of the display 1590 may face to the user (e.g., an operator or a doctor). An installation position, an installation angle, and an installation direction of the display 1590 may not be limited by the present disclosure.

In some embodiments, the installation of the display 1590 may be fixed or non-fixed.

In some embodiments, the angle, height, and direction of the display 1590 may be adjusted arbitrarily.

In some embodiments, the display 1590 may display at least one type of information such as the time information, the device information, the patient information, the image information, etc.

In some embodiments, the display 1590 may also display a current position, a target position, a target motion path, etc., of the medical device. When a deviation between the medical device and the target position is large, the display 1590 may generate a prompt message, for example, a pop-up window, a flickering screen, etc. In some embodiments, the display 1590 may also display patient registration record information, e.g., which patient the current registration record belongs to, whether a registration record of a current patient is opened or popped up, etc. When the medical device satisfies the pressure change condition, the display 1590 may also display a corresponding operation instruction, for example, closing the registration record of an unloaded patient, or popping up the registration record of the current patient to be entered.

In some embodiments, the count of the display 1590 may be one, two, or more. In some embodiments, when two or more displays are present, the displays may be disposed oppositely or arbitrarily as needed, which may not be limited in the present disclosure.

In some embodiments, the display 1590 may further include a sound playing module for playing a sound. The sound may include a music and/or a voice. By playing a music or some kind of soothing sound through the sound playing module, negative emotions such as the nervousness and panic of the patient, of the operator, and/or of the doctor may be alleviated. By playing the voice through the sound playing module, a reminder, information, etc., may be sent to the patient, the operator, and/or the doctor, so that the patient, the operator, and/or the doctor may clearly understand the detection process and precautions, which may help perform the detection process smoothly. For another example, some alarm sounds may also be played to alert the user when necessary.

In some embodiments, the display 1590 may further include an indicator, such as an indicator light or an indication information field. The indicator may be used to indicate the collision information, the status information of the display 1590, the power information of the display 1590, or the like, or any combination thereof. By adding the indicator light, the user may intuitively understand the state or power of the display 1590 and warning information during the detection process, such as warning for the collision, thereby ensuring the safety use of the medical device.

In some embodiments, the display 1590 may further include a touch screen for receiving a touch instruction input by the user. In some embodiments, the touch instruction may be used to execute one or more of: controlling the angle of the C-arm, controlling the height of the bed surface of the bed, controlling the display of the image information, adjusting the brightness of the display, controlling the display status of the touch screen, or the like, or any combination. Through the operation of the touch screen, the user may set and adjust the parameters of the medical device more directly, which improves the detection efficiency.

Figure 16:
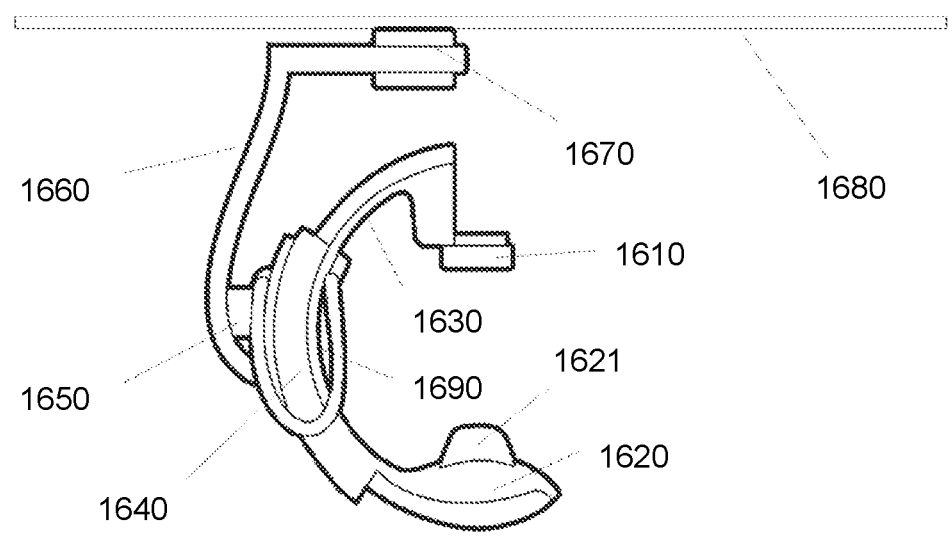
FIG. 16 is a schematic structural diagram of an exemplary medical device according to some embodiments of the present disclosure.

FIG. 16 is a schematic structural diagram illustrating an exemplary medical device according to some embodiments of the present disclosure. The medical device may be a C-arm device. Although the medical device is described by taking the C-arm device as an example herein, the medical device may be a computer tomography device, a nuclear magnetic resonance imaging device, a digital X-ray photography device, a positron emission tomography device, a single-photon emission computer tomography scanning device, a dual-mode scanning device, or the like. As shown in FIG. 16, the difference between this embodiment and the above embodiment in FIG. 15 may be that the base 1580 is not included, but a rail 1680 is disposed so that the C-arm device may be suspended and fixed. The rail 1680 may be understood as the gantry rail in FIG. 4. The C-arm device may include: a detector 1610, a radiation source 1620, a collimator 1621 disposed near the radiation source 1620, a C-arm 1630, a C-arm slide rail 1640, a connection portion 1650, a support arm 1660, a rotating column 1670, a rail 1680, and a display 1690. The display 1690 may be used to display parameter configuration information and/or operation parameter information related to the C-arm device.

In some embodiments, the support portion 1660 may be a suspension device, e.g., a boom.

In the technical solution of the embodiment of the present disclosure, by adding the display 1690 on the C-arm side of the C-arm device, information such as angle information of the C-arm 1630, height information of a bed surface, collision information, and a distance (SID) between the radiation source 1620 and an imaging surface of the detector 1610, etc., may be displayed, which may solve the problem that the display of the C-arm device is not convenient, and improve the accuracy of a C-arm motion and the safety of a detection process.

Having thus described the basic concepts, it may be rather apparent to those skilled in the art after reading this detailed disclosure that the foregoing detailed disclosure is intended to be presented by way of example only and is not limiting. Various alterations, improvements, and modifications may occur and are intended to those skilled in the art, though not expressly stated herein. These alterations, improvements, and modifications are intended to be suggested by this disclosure and are within the spirit and scope of the exemplary embodiments of this disclosure.

Moreover, certain terminology has been used to describe embodiments of the present disclosure. For example, the terms "one embodiment," "an embodiment," and/or "some embodiments" mean that a particular feature, structure, or characteristic described in connection with the embodiment is included in at least one embodiment of the present disclosure. Therefore, it is emphasized and should be appreciated that two or more references to "an embodiment" or "one embodiment" or "an alternative embodiment" in various portions of the present disclosure are not necessarily all referring to the same embodiment. Furthermore, the particular features, structures, or characteristics may be combined as suitable in one or more embodiments of the present disclosure.

Further, it will be appreciated by one skilled in the art, aspects of the present disclosure may be illustrated and described herein in any of a number of patentable classes or context including any new and useful process, machine, manufacture, or composition of matter, or any new and useful improvement thereof. Accordingly, aspects of the present disclosure may be implemented entirely hardware, entirely software (including firmware, resident software, micro-code, etc.) or combining software and hardware implementation that may all generally be referred to herein as a "unit," "module," or "system." Furthermore, aspects of the present disclosure may take the form of a computer program product embodied in one or more computer-readable media having computer-readable program code embodied thereon.

A non-transitory computer-readable signal medium may include a propagated data signal with computer readable program code embodied therein, for example, in baseband or as part of a carrier wave. Such a propagated signal may take any of a variety of forms, including electromagnetic, optical, or the like, or any suitable combination thereof. A computer-readable signal medium may be any computer-readable medium that is not a computer-readable storage medium and that may communicate, propagate, or transport a program for use by or in connection with an instruction execution system, apparatus, or device. Program code embodied on a computer-readable signal medium may be transmitted using any appropriate medium, including wireless, wireline, optical fiber cable, RF, or the like, or any suitable combination of the foregoing.

Computer program code for carrying out operations for aspects of the present disclosure may be written in any combination of one or more programming languages, including an object-oriented programming language such as Java, Scala, Smalltalk, Eiffel, JADE, Emerald, C++, C #, VB. NET, Python, or the like, conventional procedural programming languages, such as the "C" programming language, Visual Basic, Fortran, Perl, COBOL, PHP, ABAP, dynamic programming languages such as Python, Ruby, and Groovy, or other programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider) or in a cloud computing environment or offered as a service such as a Software as a Service (SaaS).

Furthermore, the recited order of processing elements or sequences, or the use of numbers, letters, or other designations, therefore, is not intended to limit the claimed processes and methods to any order except as may be specified in the claims. Although the above disclosure discusses through various examples what is currently considered to be a variety of useful embodiments of the disclosure, it is to be understood that such detail is solely for that purpose and that the appended claims are not limited to the disclosed embodiments, but, on the contrary, are intended to cover modifications and equivalent arrangements that are within the spirit and scope of the disclosed embodiments. For example, although the implementation of various components described above may be embodied in a hardware device, it may also be implemented as a software-only solution, e.g., an installation on an existing server or mobile device.

Similarly, it should be appreciated that in the foregoing description of embodiments of the present disclosure, various features are sometimes grouped together in a single embodiment, figure, or description thereof to streamline the disclosure aiding in the understanding of one or more of the various inventive embodiments. This method of disclosure, however, is not to be interpreted as reflecting an intention that the claimed object matter requires more features than are expressly recited in each claim. Rather, inventive embodiments lie in less than all features of a single foregoing disclosed embodiment.

In some embodiments, the numbers expressing quantities, properties, and so forth, used to describe and claim certain embodiments of the application are to be understood as being modified in some instances by the term "about," "approximate," or "substantially." For example, "about," "approximate" or "substantially" may indicate ±20% variation of the value it describes, unless otherwise stated. Accordingly, in some embodiments, the numerical parameters set forth in the written description and attached claims are approximations that may vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the application are approximations, the numerical values set forth in the specific examples are reported as precisely as practicable.

Each of the patents, patent applications, publications of patent applications, and other material, such as articles, books, specifications, publications, documents, things, and/or the like, referenced herein is hereby incorporated herein by this reference in its entirety for all purposes, excepting any prosecution file history associated with same, any of same that is inconsistent with or in conflict with the present document, or any of same that may have a limiting effect as to the broadest scope of the claims now or later associated with the present document. By way of example, should there be any inconsistency or conflict between the description, definition, and/or the use of a term associated with any of the incorporated material and that associated with the present document, the description, definition, and/or the use of the term in the present document shall prevail.

In closing, it is to be understood that the embodiments of the application disclosed herein are illustrative of the principles of the embodiments of the application. Other modifications that may be employed may be within the scope of the application. Thus, by way of example, but not of limitation, alternative configurations of the embodiments of the application may be utilized in accordance with the teachings herein. Accordingly, embodiments of the present application are not limited to that precisely as shown and described.

What is claimed is:

1. A motion control method for a medical device, wherein the method includes:
   obtaining a target position of a local element of the medical device, wherein the local element of medical device includes an arm configured to dispose other elements of the medical device, the target position of the medical device including a target position of the arm;
   determining a target motion path of the local element of the medical device according to a current position and the target position of the medical device, wherein the target motion path of the medical device includes a rotation path of the arm; and
   controlling the medical device to move from the current position to the target position along the target motion path.

2. The method of claim 1, wherein the medical device further includes a gantry connected to the arm, the target position of the medical equipment further including a target position of the gantry.

3. The method of claim 1, wherein obtaining the target position of the medical device is implemented through a graphical user interface (GUI) displayed on an operation console.

4. The method of claim 3, wherein the obtaining the target position through the GUI displayed on the console includes:
   determining the target position according to an operation of a device icon representing the gantry in a three-dimensional planning view, the operation including a dragging operation or a rotation operation.

5. The method of claim 1, further including:
   obtaining a prohibited operation region, wherein determining the target motion path includes:
   determining the target motion path of the medical device according to the current position, the target position, and the prohibited operation region of the medical device.

6. The method of claim 1, wherein the target position of the medical device further includes a target position of the gantry and, and the target motion path of the medical device further includes a gantry motion path.

7. The method of claim 1, wherein the other elements of the medical device include a radiation source or a flat panel detector, the target position of the medical device further includes a target position of the radiation source or a target position of the flat panel detector, and the target motion path of the medical device further includes a rotation path of the radiation source or a rotation path of the flat panel detector.

8. The method of claim 7, wherein the target position of the medical device includes a desired angular position of the radiation source or the flat panel detector, and the radiation source or the flat panel detector is adjusted to the desired angular position according to the rotation path.

9. The method of claim 1, wherein the other elements of the medical device include a display disposed on the arm, the display being configured to display parameter configuration information or operation parameter information related to the arm device.

10. The method of claim 9, wherein the parameter configuration information is used to configure the arm, and the parameter configuration information includes at least one of time information, device information, and patient information.

11. The method of claim 9, wherein the operation configuration information changes during an operation of the arm, and the operation configuration information includes at least one of angle information of the arm, height information of a bed surface, collision information, a distance between a radiation source and an imaging surface of a flat panel detector, status information of the medical device, and image information.

12. The method of claim 1, wherein the medical device further includes a bed, and the method further includes:
obtaining load change information indicating changes of related parameters of the bed generated by loading or unloading a patient; and
determining an operation instruction related to a registration record of the medical device based on the load change information and a preset change condition.

13. The method of claim 12, further comprising:
in response to that the load change information satisfies the preset change condition, determining that the operation instruction is to close a registered registration record or pop up a registration record to be entered.

14. The method of claim 12, wherein the load change information includes pressure change information, the preset change condition includes a preset pressure change condition, and
the obtaining load change information includes:
obtaining the pressure change information generated by a load change of the bed caused by loading or unloading the patient;
the determining an operation instruction related to a registration record of the medical device based on the load change information and a preset change condition includes:
when the pressure change information satisfies the preset pressure change condition, closing a registration record of an unloaded patient, or popping up a registration record for a current patient so that an information registration of the current patient can be performed.

15. The method of claim 14, wherein the preset pressure change condition includes a preset positive pressure change condition, and the determining an operation instruction related to a registration record of the medical device based on the load change information and a preset change condition includes:
when the pressure change information satisfies the preset positive pressure change condition, popping up the registration record to be entered for the current patient.

16. The method of claim 14, wherein the preset pressure change condition includes a preset negative pressure change condition, and the determining an operation instruction related to a registration record of the medical device based on the load change information and a preset change condition includes:
when the pressure change information satisfies the preset negative pressure change condition, closing a registration record for an unloaded patient.

17. The method of claim 14, wherein before obtaining the pressure change information generated by the load change of the bed caused by loading or unloading the patient, the method further includes:
obtaining weight information of the patient and determining the preset pressure change condition according to the weight information.

* * * * *